US009228196B2

(12) United States Patent
Tsay et al.

(10) Patent No.: US 9,228,196 B2
(45) Date of Patent: Jan. 5, 2016

(54) METHOD FOR CHANGING NITROGEN UTILIZATION EFFICIENCY IN PLANTS

(71) Applicant: Academia Sinica, Taipei (TW)

(72) Inventors: Yi-Fang Tsay, Taipei (TW); Shu-Chun Fan, Taipei (TW); Hui-Yu Chen, Jung Li (TW); Kuo-En Chen, Taipei (TW)

(73) Assignee: Academia Sinica, Taipei (TW)

( * ) Notice: Subject to any disclaimer, the term of this patent is extended or adjusted under 35 U.S.C. 154(b) by 266 days.

(21) Appl. No.: 14/067,317

(22) Filed: Oct. 30, 2013

(65) Prior Publication Data

US 2014/0201863 A1    Jul. 17, 2014

Related U.S. Application Data

(62) Division of application No. 12/832,234, filed on Jul. 8, 2010, now abandoned.

(60) Provisional application No. 61/223,744, filed on Jul. 8, 2009.

(51) Int. Cl.
*C12N 5/14* (2006.01)
*C12N 15/82* (2006.01)
*C07K 14/415* (2006.01)

(52) U.S. Cl.
CPC .......... *C12N 15/8243* (2013.01); *C07K 14/415* (2013.01); *C12N 15/8261* (2013.01)

(58) Field of Classification Search
None
See application file for complete search history.

(56) References Cited

U.S. PATENT DOCUMENTS

2007/0044172 A1    2/2007    Schneeberger et al.

OTHER PUBLICATIONS

Alonso, J,M et al., "Genome-Wide Insertional Mutagenesis of Arabidopsis thaliana", Science, vol. 301, (2003), pp. 653-657.
Bernfeld, P "Amylases, a and 13", Methods Enzymol., vol. 1, (1995), pp. 149-158.
Clough, S.J et al., "Floral Dip: A Simplified Method for Agrobacterium-Mediated Transformation of Arabidopsis thaliana", The Plant Journal, vol. 16, No. 6, (1998), pp. 735-743.
Deeken, R., et al., "Identification of Arabidopsis thaliana Phloem RNAs Provides a Search Criterion for Phloem-Based Transcripts Hidden in Complex Datasets of Microarray Experiments", The Plant Journal, vol. 55, (2008), pp. 746-759.
Fan et al 2009, Plant Cell 21: p. 2750-2761.
Huang, N,C et al., "Cloning and Functional Characterization of an Arabidopsis Nitrate Transporter Gene That Encodes a Constitutive Component of Low-Affinity Uptake", The Plant Cell, vol. 11, (1999), pp. 1381-1392.
Krysan, P.J et al., "T-DNA as an Insertional Mutagen in Arabidopsis", The Plant Cell, vol. 11, (1999), pp. 2283-2290.
Lagarde, D., et al., "Tissue-Specific Expression of Arabidopsis AKT1 Gene is Consistent with a Role in K+ Nutrition", The Plant Journal, vol. 9, No. 2, (1996), pp. 195-203.
Liman, E,R, et al., "Subunit Stoichiometry of a Mammalian K+ Channel Determined by Construction of Multimeric cDNAs", Neuron, vol. 9, (1992), pp. 861-871.
Lin, S-H., et al., "Mutation of the Arabidopsis NRT1.5 Nitrate Transporter Causes Defective Root-to-Shoot Nitrate Transport", The Plant Cell, vol. 20, (2008), pp. 2514-2528.
Liu, K-H., et al., "CHL1 is a Dual-Affinity Nitrate Transporter of Arabidopsis Involved in Multiple Phases of Nitrate Uptake", The Plant Cell, vol. 11, (1999), pp. 865-874.
Masclaux-Daubresse, C et al., "Leaf Nitrogen Remobilisation for Plant Development and Grain Fillin~", Plant Biology (Stutt~), vol. 10, Suppi. 1, (2008), pp. 23-36.
McAllister et al 2012, Plant Biotechnology Journal p. 1-15.
Mickelson, S., et al., "Mapping of QTL Associated with Nitrogen Storage and Remobilization in Barley (Hordeum vulgare L.) Leaves", Journal of Experimental Botany, vol. 54, No. 383, (2003), pp. 801-812.
Spindler, K.R., et al., "Analysis of Adenovirus Transforming Proteins from Early Regions 1A and 1B with Antisera to Inducible Fusion Antigens Produced in *Escherichia coil*", Journal of Virolo~y, vol. 49, No. 1, (1984), pp. 132-141.
Tsay, Y-F., et al., "The Herbicide Sensitivity Gene CHL1 of Arabidopsis Encodes a Nitrate-Inducible Nitrate Transporter", Cell, vol. 72, (1993), pp. 705-713.
Weigel, D., et al., "Activation Tagging in Arabidopsis", Plant Physiology, vol. 122, No. 4, (2000), pp. 1003-1013.
Yoo, S-D., et al., "Arabidopsis Mesophyll Protoplasts: A Versatile Cell System for Transient Gene Expression Analysis", Nature Protocols, vol. 2, No. 7, (2007), pp. 1565-1572.

*Primary Examiner* — Brent T Page
*Assistant Examiner* — Matthew Keogh
(74) *Attorney, Agent, or Firm* — Cesari and McKenna, LLP

(57) ABSTRACT

The present invention provides a method for changing nitrogen utilization efficiency in a plant comprises regulating the expression of *Arabidopsis* NRT 1.7 or an ortholog thereof so that the nitrate remobilization from older leaves to young leaves in the plant is regulated, thereby the nitrogen utilization efficiency is changed. The present invention also provides a transgenic plant obtainable by transforming a plant with an expression construct with a high or low level of expression of NRT 1.7. On the other hand, the present invention yet provides a chimera nitrate transporter, a DNA molecule coding for this chimera transporter and an expression vector thereof.

20 Claims, 12 Drawing Sheets

>ArabidopsisAt1g69870 sequence

MVLEDRKDGSSLPGRSGSFSKSSPSELDVVDPYKRISSPGSILDAEKVEKKPGGWRAVSFILGNET
LERLGSIGLLANFMVYLTKVFHLEQVDAANVINIWSGFTNLTPLVGAYISDTYVGRFKTIAFASFA
TLLGLITITLTASFPQLHPASCNSQDPLSCGGPNKLQIGVLLLGLCFLSVGSGGIRPCSIPFGVDQ
FDQRTEEGVKGVASFFNWYYMTFTVVLIITQTVVVYIQDQVSWIIGFSIPTGLMALAVVMFFAGMK
RYVYVKPEGSIFSGIAQVIVAARKKRKLKLPAEDDGTVTYYDPAIKSSVLSKLHRSNQFRCLDKAA
VVIEGDLTPEGPPADKWRLCSVQEVEEVKCLIRIVPIWSAGIISLAAMTTQGTFTVSQALKMDRNL
GPKFEIPAGSLSVISLLTIGIFLPFYDRVFVPFMRRITGHKSGITLLQRIGTGIVFAIFSMIVAGI
VERMRRIRSINAGDPTGMTPMSVFWLSPQLILMGLCEAFNIIGQIEFFNSQFPEHMRSIANSLFSL
SFAGSSYLSSFLVTVVHKFSGGHDRPDWLNKNLNAGKLDYFYYLIAVLGVVNLVYFWYCARGYRYK
VGLPIEDFEEDKSSDDVEMTSKKSMK

>ArabidopsisAt1g27080
Identities: 391/565(69%)  Positives: 461/565(81%)
>ArabidopsisAt5g28470
Identities: 227/549(41%)  Positives: 348/549(63%)
>ArabidopsisAt1g69860
Identities: 266/551(48%)  Positives: 378/551(68%)
>ArabidopsisAt1g18880
Identities: 264/572(46%)  Positives: 375/572(65%)
>ArabidopsisAt5g62680
Identities: 301/594(50%)  Positives: 394/594(66%)
>ArabidopsisAt3g47960
Identities: 280/567(49%)  Positives: 379/567(66%)
>Os04g56560
Identities: 244/581(41%)  Positives: 370/581(63%)
>Os01g68510
Identities: 289/585(49%)  Positives: 408/585(69%)
>Os07g09300
Identities: 267/597(44%)  Positives: 382/597(63%)
>Os03g48180
Identities: 288/602(48%)  Positives: 407/602(68%)
>Os12g44100
Identities: 257/584(44%)  Positives: 377/584(65%)
>Os12g44110
Identities: 275/582(47%)  Positives: 393/582(68%)
>BrassicanapusCAW77609

Fig. 11

```
Identities: 512/618(82%)  Positives: 553/618(89%)
>Vitisvinifera(grape)CAO41020
Identities: 363/621(58%)  Positives: 479/621(77%)
>RicinuscommunisEEF42210.1
Identities: 364/587(62%)  Positives: 464/587(79%)
>PopulustrichocarpaEEE90147.1
Identities: 354/546(64%)  Positives: 434/546(79%)
>Vitisvinifera(grape)XP_002276806.1gi225452684
Identities: 286/563(50%)  Positives: 396/563(70%)
>RicinuscommunisEEF45001.1gi223543470
Identities: 284/561(51%)  Positives: 398/561(71%)
>Zeamays(corn)ACN27986.1gi223947805
Identities: 291/599(49%)  Positives: 404/599(67%)
>Populustrichocarpa EEE84826.1GI:222847279
Identities: 294/641(46%)  Positives: 414/641(65%)
```

Fig. 11 (Continued)

SEQUENCE LISTING

```
<160> NUMBER OF SEQ ID NOS: 39

<210> SEQ ID NO 1
<211> LENGTH: 1863
<212> TYPE: DNA
<213> ORGANISM: Arabidopsis thaliana

<400> SEQUENCE: 1
atggttttgg aggatagaaa ggacggttct tctttgccgg gacgatccgg tagtttctct      60
aaatcgtcac cgtcggagtt ggatgttgtt gatccctaca agcggataag ttcgccggga     120
tctatattgg atgctgagaa ggtagagaaa aagcctggag gatggagagc cgtctcgttc     180 atttaggaa atgagacgct ggagagactg ggatcgatag gattgttggc aaacttcatg      240
gtttatctaa ccaaagtgtt tcacttagaa caagtcgacg ctgcaaatgt catcaacatt     300
tggtcaggtt tcaccaatct cactcctctc gtcggagcgt atatctcaga cacttatgtt     360
ggccgcttca agaccatcgc tttcgcctca ttcgccactc tcctcggact aataacaatt     420
acactcacag catcgtttcc tcaactccac ccagcatcat gcaacagcca ggacccactc     480
agttgcggcg gtccgaataa gctccagatc ggagttttgc tattgggact ctgtttcctc     540
tccgtaggga gtggaggaat acgaccttgt agcatccctt ttggggttga tcagtttgac     600
caacgaactg aggaaggggt taaggagtg gccagtttct tcaactggta ttacatgact      660
ttcactgtgg ttctgatcat tacacagacc gtagttgtgt atatccagga tcaagtcagt     720
tggattatcg gttttagtat ccctaccgga ctcatggctc ttgcggttgt tatgtttttt     780
gccggaatga agcgttatgt ctacgttaaa ccagaaggaa gtatattctc tgggatcgct     840
caagttatcg tggcagctcg taagaagcga aagctgaaac ttccggcgga agatgacggc     900
actgtcacct attacgaccc agccatcaag tctagcgtgt tatccaagtt acaccgcagt     960
```

```
aaccaattca ggtgtcttga caaagccgcg gtggttatag aaggtgacct aacacccgag    1020
ggacctcccg cagacaagtg gcggttatgc agcgtccaag aagtggaaga agtgaagtgt    1080
ttgatccgaa ttgttcctat ctggtcggcc ggaataatct cactcgcggc catgacaaca    1140
caaggcactt tcacggtctc tcaagctttg aaaatggatc gaaacttagg tcctaaattc    1200
gagattccgg ctggttcact ctccgtcatc tctctcctca caatcggcat ctttcttccc    1260
ttctacgacc gcgttttttgt accattcatg cggcgaatca ccggccataa atccggaatc    1320
acactcctcc aaaggatagg aacagggatc gttttcgcga tcttttctat gatcgttgcg    1380
ggcattgtgg agcgtatgag acgcatacgc tccatcaatg ccggagatcc aacgggaatg    1440
actccaatgt cggtgttttg gctttcgccg cagctaattc tcatgggact atgtgaagca    1500
ttcaatatca tcggacaaat tgagttcttc aacagtcagt ttccagagca catgagaagt    1560
atcgctaact ctctcttctc tttatcgttc gccggttcga gctaccttag tagttttcctt    1620 gtgactgtcg ttcataaatt ctccggtggg catgatcgtc cggattggct aaacaagaat    1680
ctcaacgcgg gaaaattgga ttacttctat tatctgattg cggttttggg tgtggttaat    1740
ctggtttact tttggtattg tgctcgggga taccggtaca aggtcggttt accgattgaa    1800
gactttgagg aggacaagtc ctccgatgat gttgagatga cttcgaagaa atcgatgaaa    1860
tga                                                                  1863

<210> SEQ ID NO 2
<211> LENGTH: 620
<212> TYPE: PRT
<213> ORGANISM: Arabidopsis thaliana

<400> SEQUENCE: 2

Met Val Leu Glu Asp Arg Lys Asp Gly Ser Ser Leu Pro Gly Arg Ser
1               5                   10                  15

Gly Ser Phe Ser Lys Ser Ser Pro Ser Glu Leu Asp Val Val Asp Pro
                20                  25                  30

Tyr Lys Arg Ile Ser Ser Pro Gly Ser Ile Leu Asp Ala Glu Lys Val
            35                  40                  45

Glu Lys Lys Pro Gly Gly Trp Arg Ala Val Ser Phe Ile Leu Gly Asn
        50                  55                  60

Glu Thr Leu Glu Arg Leu Gly Ser Ile Gly Leu Leu Ala Asn Phe Met
65                  70                  75                  80

Val Tyr Leu Thr Lys Val Phe His Leu Glu Gln Val Asp Ala Ala Asn
                85                  90                  95

Val Ile Asn Ile Trp Ser Gly Phe Thr Asn Leu Thr Pro Leu Val Gly
            100                 105                 110

Ala Tyr Ile Ser Asp Thr Tyr Val Gly Arg Phe Lys Thr Ile Ala Phe
        115                 120                 125

Ala Ser Phe Ala Thr Leu Leu Gly Leu Ile Thr Ile Thr Leu Thr Ala
    130                 135                 140

Ser Phe Pro Gln Leu His Pro Ala Ser Cys Asn Ser Gln Asp Pro Leu
145                 150                 155                 160

Ser Cys Gly Gly Pro Asn Lys Leu Gln Ile Gly Val Leu Leu Leu Gly
                165                 170                 175

Leu Cys Phe Leu Ser Val Gly Ser Gly Gly Ile Arg Pro Cys Ser Ile
            180                 185                 190

Pro Phe Gly Val Asp Gln Phe Asp Gln Arg Thr Glu Glu Gly Val Lys
        195                 200                 205
```

```
Gly Val Ala Ser Phe Phe Asn Trp Tyr Tyr Met Thr Phe Thr Val Val
    210                 215                 220

Leu Ile Ile Thr Gln Thr Val Val Tyr Ile Gln Asp Gln Val Ser
225                 230                 235                 240

Trp Ile Ile Gly Phe Ser Ile Pro Thr Gly Leu Met Ala Leu Ala Val
                245                 250                 255

Val Met Phe Phe Ala Gly Met Lys Arg Tyr Val Tyr Val Lys Pro Glu
            260                 265                 270

Gly Ser Ile Phe Ser Gly Ile Ala Gln Val Ile Val Ala Ala Arg Lys
                275                 280                 285

Lys Arg Lys Leu Lys Leu Pro Ala Glu Asp Asp Gly Thr Val Thr Tyr
290                 295                 300

Tyr Asp Pro Ala Ile Lys Ser Ser Val Leu Ser Lys Leu His Arg Ser
305                 310                 315                 320

Asn Gln Phe Arg Cys Leu Asp Lys Ala Ala Val Ile Glu Gly Asp
                325                 330                 335

Leu Thr Pro Glu Gly Pro Pro Ala Asp Lys Trp Arg Leu Cys Ser Val
                340                 345                 350

Gln Glu Val Glu Glu Val Lys Cys Leu Ile Arg Ile Val Pro Ile Trp
                355                 360                 365

Ser Ala Gly Ile Ile Ser Leu Ala Ala Met Thr Thr Gln Gly Thr Phe
    370                 375                 380

Thr Val Ser Gln Ala Leu Lys Met Asp Arg Asn Leu Gly Pro Lys Phe
385                 390                 395                 400

Glu Ile Pro Ala Gly Ser Leu Ser Val Ile Ser Leu Leu Thr Ile Gly
                405                 410                 415

Ile Phe Leu Pro Phe Tyr Asp Arg Val Phe Val Pro Phe Met Arg Arg
                420                 425                 430

Ile Thr Gly His Lys Ser Gly Ile Thr Leu Leu Gln Arg Ile Gly Thr
            435                 440                 445

Gly Ile Val Phe Ala Ile Phe Ser Met Ile Val Ala Gly Ile Val Glu
    450                 455                 460

Arg Met Arg Arg Ile Arg Ser Ile Asn Ala Gly Asp Pro Thr Gly Met
465                 470                 475                 480

Thr Pro Met Ser Val Phe Trp Leu Ser Pro Gln Leu Ile Leu Met Gly
                485                 490                 495

Leu Cys Glu Ala Phe Asn Ile Ile Gly Gln Ile Glu Phe Phe Asn Ser
            500                 505                 510

Gln Phe Pro Glu His Met Arg Ser Ile Ala Asn Ser Leu Phe Ser Leu
                515                 520                 525

Ser Phe Ala Gly Ser Ser Tyr Leu Ser Ser Phe Leu Val Thr Val Val
    530                 535                 540

His Lys Phe Ser Gly Gly His Asp Arg Pro Asp Trp Leu Asn Lys Asn
545                 550                 555                 560

Leu Asn Ala Gly Lys Leu Asp Tyr Phe Tyr Tyr Leu Ile Ala Val Leu
                565                 570                 575

Gly Val Val Asn Leu Val Tyr Phe Trp Tyr Cys Ala Arg Gly Tyr Arg
            580                 585                 590

Tyr Lys Val Gly Leu Pro Ile Glu Asp Phe Glu Glu Asp Lys Ser Ser
                595                 600                 605

Asp Asp Val Glu Met Thr Ser Lys Lys Ser Met Lys
610                 615                 620
```

<210> SEQ ID NO 3
<211> LENGTH: 1366
<212> TYPE: DNA
<213> ORGANISM: Arabidopsis thaliana

<400> SEQUENCE: 3

| | | | | | | |
|---|---|---|---|---|---|---|
| tctagataaa | catatgtacc | acacattcga | gcaatcgtat | aaaattatat | acgaataaat | 60 |
| agaattagtt | tctttctcgg | aaattctgtt | aatattttta | ggaggattaa | gtgggttcga | 120 |
| aatttaatca | cttcctgcac | aaattcatct | caatgtatta | attggtgata | tgtcattttt | 180 |
| ttatttatt | ttttggtatg | agcttccaaa | gttttaaggc | cagctctata | tgtgtactat | 240 |
| tgtttctaac | tttattatat | taaattttgg | tgatatgtgt | ttctttgttt | gattgcaacc | 300 |
| caaaatagtt | taaggttcat | cttagagtgc | gatgactttt | tgtgcaaaaa | tattagatca | 360 |
| tgttggtatg | tacgttttga | gttttatta | tttgtttacc | aattgaacga | ctctcaacaa | 420 |
| gcaattgtat | gccaagatga | catattggac | gtttcaagtg | tgtgaattgt | ataaagcagt | 480 |
| aaataaaatc | tactcttatt | aactagtttg | aaagagagtt | ttaacttcga | agaatctatc | 540 |
| gccatgagtc | aaaatcgtat | aaatgtgaca | aatgtttatc | tctatcaata | atagtaaaaa | 600 |
| ttttaaaagg | ttctatataa | attttaagat | tttgtcagga | tcattaaagt | gtagaactaa | 660 |
| gtcaactgat | tgattaatag | aaaaaatcga | tacaatctca | cttcctttaa | gaaaataaaa | 720 |
| ataaatatg | ctttagagaa | aataaaatct | cgcttattta | tgagatatca | tatcattttt | 780 |
| aggtaaaaaa | gattagatgt | cctttgaga | cacatcatac | catatatatg | accgacaaca | 840 |
| cacataaaac | cgcgtgaaca | aaaaatatca | tccatcaacc | ccttacgatg | caaatgtact | 900 |
| gtaaaagatg | gttcattaat | ttaacatcgt | attttaacgt | tacaattgta | tggaacatgg | 960 |
| aaggttcaca | atacgtggaa | caaaacaata | atgttacgta | cggtgtaaga | aaaacaaaaa | 1020 |
| aaacatagca | ctaaaatagt | tttcttttaa | ttttcctctt | caaacttctc | acgtggaggc | 1080 |
| tactagtggc | gaacgtcatt | caaatttacc | cacaccccacc | atatattatc | tactcactcc | 1140 |
| cttatatata | cacacttcca | caaataattc | actacaccca | aaaaagcttc | taacaaagag | 1200 |
| aaagtgtctg | tatgttgtgc | ccactctcta | catttatcaa | tcacttcatg | tgtgttacct | 1260 |
| tgattgcaaa | aaagtgagaa | tatattctca | caacattaaa | tccaccccga | aatcgaagtg | 1320 |
| agtatatcac | gagtgtagta | atatcttaga | gatgaggatc | cagatg | | 1366 |

<210> SEQ ID NO 4
<211> LENGTH: 1286
<212> TYPE: DNA
<213> ORGANISM: Arabidopsis thaliana

<400> SEQUENCE: 4

| | | | | | | |
|---|---|---|---|---|---|---|
| ggatccccaa | catggtggag | cacgacactc | tcgtctactc | caagaatatc | aaagatacag | 60 |
| tctcagaaga | ccagagggct | attgagactt | ttcaacaaag | ggtaatatcg | ggaaacctcc | 120 |
| tcggattcca | ttgcccagct | atctgtcact | tcatcgaaag | gacagtagaa | aggaagatg | 180 |
| gcttctacaa | atgccatcat | tgcgataaag | gaaaggctat | cgttcaagat | gcctctaccg | 240 |
| acagtggtcc | caaagatgga | cccccaccca | cgaggaacat | cgtggaaaaa | gaagacgttc | 300 |
| caaccacgtc | ttcaaagcaa | gtggattgat | gtgatatcta | gatccccaac | atggtggagc | 360 |
| acgacactct | cgtctactcc | aagaatatca | aagatacagt | ctcagaagac | cagagggcta | 420 |
| ttgagacttt | tcaacaaagg | gtaatatcgg | gaaacctcct | cggattccat | tgcccagcta | 480 |
| tctgtcactt | catcgaaagg | acagtagaaa | aggaagatgg | cttctacaaa | tgccatcatt | 540 |

```
gcgataaagg aaaggctatc gttcaagatg cctctaccga cagtggtccc aaagatggac      600
ccccacccac gaggaacatc gtggaaaaag aagacgttcc aaccacgtct tcaaagcaag      660
tggattgatg tgatatctag atccccaaca tggtggagca cgacactctc gtctactcca      720
agaatatcaa agatacagtc tcagaagacc agagggctat tgagactttt caacaaaggg      780
taatatcggg aaacctcctc ggattccatt gcccagctat ctgtcacttc atcgaaagga      840
cagtagaaaa ggaagatggc ttctacaaat gccatcattg cgataaagga aggctatcg       900 ttcaagatgc ctctaccgac agtggtccca agatggaccc cacccacg aggaacatcg        960 tggaaaaaga agacgttcca accacgtctt caaagcaagt ggattgatgt gatatctaga     1020
tccccaacat ggtggagcac gacactctcg tctactccaa gaatatcaaa gatacagtct     1080
cagaagacca gagggctatt gagactttc aacaaagggt aatatcggga aacctcctcg      1140
gattccattg cccagctatc tgtcacttca tcgaaaggac agtagaaaag gaagatggct     1200
tctacaaatg ccatcattgc gataaaggaa aggctatcgt tcaagatgcc tctaccgaca     1260
gtggtcccaa agatggaccc ccaccc                                          1286

<210> SEQ ID NO 5

<400> SEQUENCE: 5

000

<210> SEQ ID NO 6
<211> LENGTH: 1773
<212> TYPE: DNA
<213> ORGANISM: Arabidopsis thaliana

<400> SEQUENCE: 6
atgtctcttc ctgaaactaa atctgatgat atccttcttg atgcttggga cttccaaggc       60
cgtcccgccg atcgctcaaa aaccggcggc tgggccagcg ccgccatgat tctttgtatt      120
gaggccgtgg agaggctgac gacgttaggt atcggagtta atctggtgac gtatttgacg      180
ggaactatgc atttaggcaa tgcaactgcg gctaacaccg ttaccaattt cctcggaact      240
tctttcatgc tctgtctcct cggtggcttc atcgccgata cctttctcgg caggtaccta      300
acgattgcta tattcgccgc aatccaagcc acgggtgttt caatcttaac tctatcaaca      360
atcataccgg gacttcgacc accaagatgc aatccaacaa cgtcgtctca ctgcgaacaa      420
gcaagtggaa tacaactgac ggtcctatac ttagccttat acctcaccgc tctaggaacg      480
ggaggcgtga aggctagtgt ctcgggtttc gggtcggacc aattcgatga gaccgaacca      540
aaagaacgat cgaaaatgac atatttcttc aaccgtttct tcttttgtat caacgttggc      600
tctcttttag ctgtgacggt ccttgtctac gtacaagacg atgttggacg caaatggggc      660
tatggaattt gcgcgtttgc gatcgtgctt gcactcagcg ttttcttggc cggaacaaac      720
cgctaccgtt tcaagaagtt gatcggtagc ccgatgacgc aggttgctgc ggttatcgtg      780
gcggcgtgga ggaataggaa gctcgagctg ccggcagatc cgtcctatct ctacgatgtg      840
gatgatatta ttgcggcgga aggttcgatg aagggtaaac aaaagctgcc acacactgaa      900
caattccgtt cattagataa ggcagcaata agggatcagg aagcgggagt tacctcgaat      960
gtattcaaca gtggacact ctcaacacta acagatgttg aggaagtgaa acaaatcgtg      1020
cgaatgttac caatttgggc aacatgcatc ctccttctgga ccgtccacgc tcaattaacg     1080
acattatcag tcgcacaatc cgagacattg gaccgttcca tcgggagctt cgagatccct     1140
```

```
ccagcatcga tggcagtctt ctacgtcggt ggcctcctcc taaccaccgc cgtctatgac      1200
cgcgtcgcca ttcgtctatg caaaaagcta ttcaactacc cccatggtct aagaccgctt      1260
caacggatcg gtttggggct tttcttcgga tcaatggcta tggctgtggc tgctttggtc      1320
gagctcaaac gtcttagaac tgcacacgct catggtccaa cagtcaaaac gcttcctcta      1380
gggttttatc tactcatccc acaatatctt attgtcggta tcggcgaagc gttaatctac      1440
acaggacagt tagatttctt cttgagagag tgccctaaag gtatgaaagg gatgagcacg      1500
ggtctattgt tgagcacatt ggcattaggc tttttcttca gctcggttct cgtgacaatc      1560
gtcgagaaat tcaccgggaa agctcatcca tggattgccg atgatctcaa caagggccgt      1620
ctttacaatt tctactggct tgtggccgta cttgttgcct tgaacttcct cattttccta      1680
gttttctcca gtggtacgt ttacaaggaa aaaagactag ctgaggtggg gattgagttg      1740
gatgatgagc cgagtattcc aatgggtcat tga                                  1773
```

```
<210> SEQ ID NO 7
<211> LENGTH: 590
<212> TYPE: PRT
<213> ORGANISM: Arabidopsis thaliana

<400> SEQUENCE: 7

Met Ser Leu Pro Glu Thr Lys Ser Asp Asp Ile Leu Leu Asp Ala Trp
1               5                   10                  15

Asp Phe Gln Gly Arg Pro Ala Asp Arg Ser Lys Thr Gly Gly Trp Ala
                20                  25                  30

Ser Ala Ala Met Ile Leu Cys Ile Glu Ala Val Glu Arg Leu Thr Thr
            35                  40                  45

Leu Gly Ile Gly Val Asn Leu Val Thr Tyr Leu Thr Gly Thr Met His
        50                  55                  60

Leu Gly Asn Ala Thr Ala Ala Asn Thr Val Thr Asn Phe Leu Gly Thr
65                  70                  75                  80

Ser Phe Met Leu Cys Leu Leu Gly Gly Phe Ile Ala Asp Thr Phe Leu
                85                  90                  95

Gly Arg Tyr Leu Thr Ile Ala Ile Phe Ala Ala Ile Gln Ala Thr Gly
                100                 105                 110

Val Ser Ile Leu Thr Leu Ser Thr Ile Ile Pro Gly Leu Arg Pro Pro
            115                 120                 125

Arg Cys Asn Pro Thr Thr Ser Ser His Cys Glu Gln Ala Ser Gly Ile
        130                 135                 140

Gln Leu Thr Val Leu Tyr Leu Ala Leu Tyr Leu Thr Ala Leu Gly Thr
145                 150                 155                 160

Gly Gly Val Lys Ala Ser Val Ser Gly Phe Gly Ser Asp Gln Phe Asp
                165                 170                 175

Glu Thr Glu Pro Lys Glu Arg Ser Lys Met Thr Tyr Phe Phe Asn Arg
                180                 185                 190

Phe Phe Phe Cys Ile Asn Val Gly Ser Leu Leu Ala Val Thr Val Leu
            195                 200                 205

Val Tyr Val Gln Asp Asp Val Gly Arg Lys Trp Gly Tyr Gly Ile Cys
        210                 215                 220

Ala Phe Ala Ile Val Leu Ala Leu Ser Val Phe Leu Ala Gly Thr Asn
225                 230                 235                 240

Arg Tyr Arg Phe Lys Lys Leu Ile Gly Ser Pro Met Thr Gln Val Ala
                245                 250                 255

Ala Val Ile Val Ala Ala Trp Arg Asn Arg Lys Leu Glu Leu Pro Ala
```

```
                 260                 265                 270
Asp Pro Ser Tyr Leu Tyr Asp Val Asp Ile Ile Ala Ala Glu Gly
            275                 280                 285

Ser Met Lys Gly Lys Gln Lys Leu Pro His Thr Glu Gln Phe Arg Ser
        290                 295                 300

Leu Asp Lys Ala Ala Ile Arg Asp Gln Glu Ala Gly Val Thr Ser Asn
305                 310                 315                 320

Val Phe Asn Lys Trp Thr Leu Ser Thr Leu Thr Asp Val Glu Glu Val
                325                 330                 335

Lys Gln Ile Val Arg Met Leu Pro Ile Trp Ala Thr Cys Ile Leu Phe
            340                 345                 350

Trp Thr Val His Ala Gln Leu Thr Thr Leu Ser Val Ala Gln Ser Glu
        355                 360                 365

Thr Leu Asp Arg Ser Ile Gly Ser Phe Glu Ile Pro Pro Ala Ser Met
    370                 375                 380

Ala Val Phe Tyr Val Gly Gly Leu Leu Leu Thr Thr Ala Val Tyr Asp
385                 390                 395                 400

Arg Val Ala Ile Arg Leu Cys Lys Lys Leu Phe Asn Tyr Pro His Gly
                405                 410                 415

Leu Arg Pro Leu Gln Arg Ile Gly Leu Gly Leu Phe Phe Gly Ser Met
            420                 425                 430

Ala Met Ala Val Ala Ala Leu Val Glu Leu Lys Arg Leu Arg Thr Ala
        435                 440                 445

His Ala His Gly Pro Thr Val Lys Thr Leu Pro Leu Gly Phe Tyr Leu
    450                 455                 460

Leu Ile Pro Gln Tyr Leu Ile Val Gly Ile Gly Glu Ala Leu Ile Tyr
465                 470                 475                 480

Thr Gly Gln Leu Asp Phe Phe Leu Arg Glu Cys Pro Lys Gly Met Lys
                485                 490                 495

Gly Met Ser Thr Gly Leu Leu Leu Ser Thr Leu Ala Leu Gly Phe Phe
            500                 505                 510

Phe Ser Ser Val Leu Val Thr Ile Val Glu Lys Phe Thr Gly Lys Ala
        515                 520                 525

His Pro Trp Ile Ala Asp Asp Leu Asn Lys Gly Arg Leu Tyr Asn Phe
    530                 535                 540

Tyr Trp Leu Val Ala Val Leu Val Ala Leu Asn Phe Leu Ile Phe Leu
545                 550                 555                 560

Val Phe Ser Lys Trp Tyr Val Tyr Lys Glu Lys Arg Leu Ala Glu Val
                565                 570                 575

Gly Ile Glu Leu Asp Asp Glu Pro Ser Ile Pro Met Gly His
            580                 585                 590

<210> SEQ ID NO 8
<211> LENGTH: 1758
<212> TYPE: DNA
<213> ORGANISM: Arabidopsis thaliana

<400> SEQUENCE: 8
atggaagtgg aagaagaggt ctcaagatgg gaaggctacg ccgattggag aaacagagca      60
gccgtgaaag gcgtcacgg tggcatgctc ccgcctctct tcgtcttagt ggtggagata     120
ttagagaatc tagcgtattt ggcgaatgcg agtaatcttg tgctataccT aagagaatac     180
atgcacatgt ctccatcaaa atcggcaaat gacgtcacca atttcatggg cacagctttt     240
ctcctagctc tcctcggtgg tttcctctcc gacgctttct tctccacttt tcaaatcttc     300
```

```
ctcatctcag cttccatcga gtttttggga ttgatcatac tcacaattca agctcggaca    360
ccatccttaa tgcctccatc gtgcgatagt cccacatgtg aagaagtgag tggttcgaag    420
gcagcgatgc tattcgtggg gttgtacctt gtagctttgg gtgtgggagg gatcaaaggt    480
tcattagcat ctcacggagc agaacagttt gatgagagta cacctaaagg tcggaaacaa    540
aggtcaacgt tctttaacta cttcgtgttt tgtcttgctt gtggagcact agttgctgtc    600
acgtttgtag tttggttaga agacaacaaa ggatgggaat ggggattcgg tgtttctacc    660
attgctatct tcgtctctat tctcatcttt ctctctggat caagatttta taggaacaag    720
attccatgtg gaagtcctct caccacaatc ttgaaggttc ttcttgcggc ttcggttaag    780
tgctgctcga gtggaagttc aagcaatgcg gttgcgagta tgtccgtgag tccctcaaat    840
cattgcgtat caaggggaa aaagaagtt gaatcacaag gagaattgga aaagccacgt    900
caagaagaag ctttgcctcc tcgggcacaa ctaactaaca gtttgaaagt attaaatgga    960 gctgcgatg aaaaacctgt ccatagattg ttagaatgca cagtccaaca agtggaagat   1020
gtgaagattg tcttgaaaat gcttccgata tttgcttgca ctatcatgct taactgttgc   1080
ttagctcagc tctctacatt ctccgtccaa caagctgctt ccatgaacac aaagatagga   1140
agcctaaaga tacctccagc ttccttaccg atcttccccg tcgttttcat aatgatcctc   1200
gcacctatct acgaccatct cattatccca ttcgctagaa aagctaccaa gaccgaaaca   1260
ggagtcactc atctacaaag aatcggagta ggtttagttc tttcgatatt agcaatggcg   1320
gttgcagctc tagttgagat taaacgaaag ggagtggcta agactccgg cttgcttgac   1380 tcgaagaaa ccttacccgt gactttccta tggatcgcac ttcagtatct tttcctaggg   1440
tcagccgatc tattcacact agctggacta ctagagtatt tcttcacgga agcaccttcc   1500
tcaatgagat ctctcgcaac atcgctctcg tgggcttctt tggctatggg gtattaccta   1560
agctcagtga tcgtgtccat agtaaacagc atcacaggaa gctcagggaa cacaccttgg   1620
ctcagaggaa aaagcataaa ccgttacaaa ctagactact tctattggct aatgtgtgtt   1680
cttagtgcag ctaacttctt gcactacctc ttttgggcaa tgcgttacaa gtatagatca   1740
actggttcaa gaagctaa                                                 1758
```

<210> SEQ ID NO 9
<211> LENGTH: 585
<212> TYPE: PRT
<213> ORGANISM: Arabidopsis thaliana

<400> SEQUENCE: 9

```
Met Glu Val Glu Glu Val Ser Arg Trp Glu Gly Tyr Ala Asp Trp
1               5                   10                  15

Arg Asn Arg Ala Ala Val Lys Gly Arg His Gly Met Leu Ala Ala
                20                  25                  30

Ser Phe Val Leu Val Val Glu Ile Leu Glu Asn Leu Ala Tyr Leu Ala
            35                  40                  45

Asn Ala Ser Asn Leu Val Leu Tyr Leu Arg Glu Tyr Met His Met Ser
    50                  55                  60

Pro Ser Lys Ser Ala Asn Asp Val Thr Asn Phe Met Gly Thr Ala Phe
65                  70                  75                  80

Leu Leu Ala Leu Leu Gly Gly Phe Leu Ser Asp Ala Phe Ser Thr
                85                  90                  95

Phe Gln Ile Phe Leu Ile Ser Ala Ser Ile Glu Phe Leu Gly Leu Ile
            100                 105                 110
```

-continued

```
Ile Leu Thr Ile Gln Ala Arg Thr Pro Ser Leu Met Pro Pro Ser Cys
        115                 120                 125

Asp Ser Pro Thr Cys Glu Glu Val Ser Gly Ser Lys Ala Ala Met Leu
130                 135                 140

Phe Val Gly Leu Tyr Leu Val Ala Leu Gly Val Gly Ile Lys Gly
145                 150                 155                 160

Ser Leu Ala Ser His Gly Ala Glu Gln Phe Asp Glu Ser Thr Pro Lys
                165                 170                 175

Gly Arg Lys Gln Arg Ser Thr Phe Phe Asn Tyr Phe Val Phe Cys Leu
            180                 185                 190

Ala Cys Gly Ala Leu Val Ala Val Thr Phe Val Val Trp Leu Glu Asp
        195                 200                 205

Asn Lys Gly Trp Glu Trp Gly Phe Gly Val Ser Thr Ile Ala Ile Phe
210                 215                 220

Val Ser Ile Leu Ile Phe Leu Ser Gly Ser Arg Phe Tyr Arg Asn Lys
225                 230                 235                 240

Ile Pro Cys Gly Ser Pro Leu Thr Thr Ile Leu Lys Val Leu Leu Ala
                245                 250                 255

Ala Ser Val Lys Cys Cys Ser Ser Gly Ser Ser Asn Ala Val Ala
            260                 265                 270

Ser Met Ser Val Ser Pro Ser Asn His Cys Val Ser Lys Gly Lys Lys
        275                 280                 285

Glu Val Glu Ser Gln Gly Glu Leu Glu Lys Pro Arg Gln Glu Glu Ala
290                 295                 300

Leu Pro Pro Arg Ala Gln Leu Thr Asn Ser Leu Lys Val Leu Asn Gly
305                 310                 315                 320

Ala Ala Asp Glu Lys Pro Val His Arg Leu Leu Glu Cys Thr Val Gln
                325                 330                 335

Gln Val Glu Asp Val Lys Ile Val Leu Lys Met Leu Pro Ile Phe Ala
            340                 345                 350

Cys Thr Ile Met Leu Asn Cys Cys Leu Ala Gln Leu Ser Thr Phe Ser
        355                 360                 365

Val Gln Gln Ala Ala Ser Met Asn Thr Lys Ile Gly Ser Leu Lys Ile
370                 375                 380

Pro Pro Ala Ser Leu Pro Ile Phe Pro Val Val Phe Ile Met Ile Leu
385                 390                 395                 400

Ala Pro Ile Tyr Asp His Leu Ile Ile Pro Phe Ala Arg Lys Ala Thr
                405                 410                 415

Lys Thr Glu Thr Gly Val Thr His Leu Gln Arg Ile Gly Val Gly Leu
            420                 425                 430

Val Leu Ser Ile Leu Ala Met Ala Val Ala Ala Leu Val Glu Ile Lys
        435                 440                 445

Arg Lys Gly Val Ala Lys Asp Ser Gly Leu Leu Asp Ser Lys Glu Thr
450                 455                 460

Leu Pro Val Thr Phe Leu Trp Ile Ala Leu Gln Tyr Leu Phe Leu Gly
465                 470                 475                 480

Ser Ala Asp Leu Phe Thr Leu Ala Gly Leu Leu Glu Tyr Phe Phe Thr
                485                 490                 495

Glu Ala Pro Ser Ser Met Arg Ser Leu Ala Thr Ser Leu Ser Trp Ala
            500                 505                 510

Ser Leu Ala Met Gly Tyr Tyr Leu Ser Ser Val Ile Val Ser Ile Val
        515                 520                 525
```

```
Asn Ser Ile Thr Gly Ser Ser Gly Asn Thr Pro Trp Leu Arg Gly Lys
530                 535                 540

Ser Ile Asn Arg Tyr Lys Leu Asp Tyr Phe Tyr Trp Leu Met Cys Val
545                 550                 555                 560

Leu Ser Ala Ala Asn Phe Leu His Tyr Leu Phe Trp Ala Met Arg Tyr
                565                 570                 575

Lys Tyr Arg Ser Thr Gly Ser Arg Ser
            580                 585

<210> SEQ ID NO 10
<211> LENGTH: 1767
<212> TYPE: DNA
<213> ORGANISM: Arabidopsis thaliana

<400> SEQUENCE: 10
atggaagtgg aagaagaggt ctcaagatgg gaaggctacg ccgattggag aaacagagca       60
gccgtgaaag gccgtcacgg tggcatgctc gccgcctctt cgtcttagt ggtggagata      120 ttagagaatc tagcgtattt ggcgaatgcg agtaatcttg tgctatacct aagagaatac    180
atgcacatgt ctccatcaaa atcggcaaat gacgtcacca atttcctcgg aacttctttc    240
atgctctgtc tcctcggtgg cttcatcgcc gatacctttc tcggcaggta cctaacgatt    300
gctatattcg ccgcaatcca agccacgggt gtttcaatct taactctatc aacaatcata    360
ccgggacttc gaccaccaag atgcaatcca acaacgtcgt ctcactgcga caagcaagt    420 ggaatacaac tgacggtcct atacttagcc ctataccca ccgctctagg aacgggaggc    480
gtgaaggcta gtgtctcggg tttcgggtcg gaccaattcg atgagaccga accaaaagaa    540
cgatcgaaaa tgacatattt cttcaaccgt ttcttctttt gtatcaacgt tggcgcacta    600
gttgctgtca cgtttgtagt ttggttagaa gacaacaaag gatgggaatg gggattcggt    660
gtttctacca ttgctatctt cgtctctatt ctcatctttc tctctggatc aagattttat    720
aggaacaaga ttccatgtgg aagtcctctc accacaatct tgaaggttct tcttgcggct    780

tcggttaagt gctgctcgag tggaagttca agcaatgcgg ttgcgagtat gтccgтgагт    840 ccctcaaatc attgcgtatc aaaggggaaa aagaagttg aatcacaagg agaattggaa    900
aagccacgtc aagaagaagc tttgcctcct cgggcacaac taactaacag tttgaaagta    960

ttaaatggag ctgcggatga aaaacctgtc catagattgt tagaatgcac agtccaacaa   1020
gtggaagatg tgaagattgt cttgaaaatg cttccgatat tgcttgcac tatcatgctt   1080 aactgttgct agctcagct ctctacattc tccgtccaac aagctgcttc catgaacaca   1140
aagataggaa gcctaaagat acctccagct tccttaccga tcttccccgt cgтттттcатa   1200

atgatcctcg cacctatcta cgaccatctc attatcccat tcgctagaaa agctaccaag   1260
accgaaacag gагтcacтca tctacaaaga atcggagtag gтттagтттcт ttcgatatta   1320 gcaatggcgg ttgcagctct agttgagatt aaacgaaagg gагтggcтaa agactccggc   1380

ttgcttgact cgaaagaaac cttacccgtg acttccctat ggatcgcact tcagtatctt   1440

ttcctagggt cagccgatct attcacacta gctggactac тagагтаттт cttcacggaa   1500 gcaccttcct caatgagatc tctcgcaaca tcgctctcgt gggcttcttt ggctatgggg   1560

tattacctaa gctcagtgat cgtgtccata gtaaacagca tcacaggaag ctcagggaac   1620
acaccttggc tcagaggaaa aagcataaac cgttacaaac tagactactt ctattggcta   1680

atgtgtgttc ттaгтgcagc taacttcttg cactacctct tttgggcaat gcgttacaag   1740

tatagatcaa стgгтtcaag aagctaa                                        1767
```

<210> SEQ ID NO 11
<211> LENGTH: 588
<212> TYPE: PRT
<213> ORGANISM: Arabidopsis thaliana

<400> SEQUENCE: 11

```
Met Glu Val Glu Glu Val Ser Arg Trp Glu Gly Tyr Ala Asp Trp
1               5                   10                  15

Arg Asn Arg Ala Ala Val Lys Gly Arg His Gly Gly Met Leu Ala Ala
            20                  25                  30

Ser Phe Val Leu Val Val Glu Ile Leu Glu Asn Leu Ala Tyr Leu Ala
        35                  40                  45

Asn Ala Ser Asn Leu Val Leu Tyr Leu Arg Glu Tyr Met His Met Ser
        50                  55                  60

Pro Ser Lys Ser Ala Asn Asp Val Thr Asn Phe Leu Gly Thr Ser Phe
65                  70                  75                  80

Met Leu Cys Leu Leu Gly Gly Phe Ile Ala Asp Thr Phe Leu Gly Arg
                85                  90                  95

Tyr Leu Thr Ile Ala Ile Phe Ala Ala Ile Gln Ala Thr Gly Val Ser
            100                 105                 110

Ile Leu Thr Leu Ser Thr Ile Ile Pro Gly Leu Arg Pro Pro Arg Cys
        115                 120                 125

Asn Pro Thr Thr Ser Ser His Cys Glu Gln Ala Ser Gly Ile Gln Leu
        130                 135                 140

Thr Val Leu Tyr Leu Ala Leu Tyr Leu Thr Ala Leu Gly Thr Gly Gly
145                 150                 155                 160

Val Lys Ala Ser Val Ser Gly Phe Gly Ser Asp Gln Phe Asp Glu Thr
                165                 170                 175

Glu Pro Lys Glu Arg Ser Lys Met Thr Tyr Phe Phe Asn Arg Phe Phe
            180                 185                 190

Phe Cys Ile Asn Val Gly Ala Leu Val Ala Val Thr Phe Val Val Trp
        195                 200                 205

Leu Glu Asp Asn Lys Gly Trp Glu Trp Gly Phe Gly Val Ser Thr Ile
        210                 215                 220

Ala Ile Phe Val Ser Ile Leu Ile Phe Leu Ser Gly Ser Arg Phe Tyr
225                 230                 235                 240

Arg Asn Lys Ile Pro Cys Gly Ser Pro Leu Thr Thr Ile Leu Lys Val
                245                 250                 255

Leu Leu Ala Ala Ser Val Lys Cys Cys Ser Ser Gly Ser Ser Ser Asn
            260                 265                 270

Ala Val Ala Ser Met Ser Val Ser Pro Ser Asn His Cys Val Ser Lys
        275                 280                 285

Gly Lys Lys Glu Val Glu Ser Gln Gly Glu Leu Glu Lys Pro Arg Gln
        290                 295                 300

Glu Glu Ala Leu Pro Pro Arg Ala Gln Leu Thr Asn Ser Leu Lys Val
305                 310                 315                 320

Leu Asn Gly Ala Ala Asp Glu Lys Pro Val His Arg Leu Leu Glu Cys
                325                 330                 335

Thr Val Gln Gln Val Glu Asp Val Lys Ile Val Leu Lys Met Leu Pro
            340                 345                 350

Ile Phe Ala Cys Thr Ile Met Leu Asn Cys Cys Leu Ala Gln Leu Ser
        355                 360                 365

Thr Phe Ser Val Gln Gln Ala Ala Ser Met Asn Thr Lys Ile Gly Ser
```

```
                     370             375             380
Leu Lys Ile Pro Pro Ala Ser Leu Pro Ile Phe Pro Val Val Phe Ile
385                 390                 395                 400

Met Ile Leu Ala Pro Ile Tyr Asp His Leu Ile Ile Pro Phe Ala Arg
                405                 410                 415

Lys Ala Thr Lys Thr Glu Thr Gly Val Thr His Leu Gln Arg Ile Gly
            420                 425                 430

Val Gly Leu Val Leu Ser Ile Leu Ala Met Ala Val Ala Ala Leu Val
        435                 440                 445

Glu Ile Lys Arg Lys Gly Val Ala Lys Asp Ser Gly Leu Leu Asp Ser
    450                 455                 460

Lys Glu Thr Leu Pro Val Thr Phe Leu Trp Ile Ala Leu Gln Tyr Leu
465                 470                 475                 480

Phe Leu Gly Ser Ala Asp Leu Phe Thr Leu Ala Gly Leu Leu Glu Tyr
                485                 490                 495

Phe Phe Thr Glu Ala Pro Ser Ser Met Arg Ser Leu Ala Thr Ser Leu
                500                 505                 510

Ser Trp Ala Ser Leu Ala Met Gly Tyr Tyr Leu Ser Ser Val Ile Val
        515                 520                 525

Ser Ile Val Asn Ser Ile Thr Gly Ser Ser Gly Asn Thr Pro Trp Leu
530                 535                 540

Arg Gly Lys Ser Ile Asn Arg Tyr Lys Leu Asp Tyr Phe Tyr Trp Leu
545                 550                 555                 560

Met Cys Val Leu Ser Ala Ala Asn Phe Leu His Tyr Leu Phe Trp Ala
                565                 570                 575

Met Arg Tyr Lys Tyr Arg Ser Thr Gly Ser Arg Ser
                580                 585

<210> SEQ ID NO 12
<211> LENGTH: 29
<212> TYPE: DNA
<213> ORGANISM: Artificial Sequence
<220> FEATURE:
<223> OTHER INFORMATION: primer

<400> SEQUENCE: 12
ccacacccac catatattat ctactcact                                             29

<210> SEQ ID NO 13
<211> LENGTH: 25
<212> TYPE: DNA
<213> ORGANISM: Artificial Sequence
<220> FEATURE:
<223> OTHER INFORMATION: primer

<400> SEQUENCE: 13
gaattctaat ggttttggag gatag                                                 25

<210> SEQ ID NO 14
<211> LENGTH: 23
<212> TYPE: DNA
<213> ORGANISM: Artificial Sequence
<220> FEATURE:
<223> OTHER INFORMATION: primer

<400> SEQUENCE: 14 aagcttttc tctaccttct cag                                                    23

<210> SEQ ID NO 15
```

```
<211> LENGTH: 20
<212> TYPE: DNA
<213> ORGANISM: Artificial Sequence
<220> FEATURE:
<223> OTHER INFORMATION: primer

<400> SEQUENCE: 15
aaccactgga ggagtcaaga                                               20

<210> SEQ ID NO 16
<211> LENGTH: 21
<212> TYPE: DNA
<213> ORGANISM: Artificial Sequence
<220> FEATURE:
<223> OTHER INFORMATION: primer

<400> SEQUENCE: 16
caattaagca cgttctcctc t                                             21

<210> SEQ ID NO 17
<211> LENGTH: 24
<212> TYPE: DNA
<213> ORGANISM: Artificial Sequence
<220> FEATURE:
<223> OTHER INFORMATION: primer

<400> SEQUENCE: 17
caacagtcag tttccagagc acat                                          24

<210> SEQ ID NO 18
<211> LENGTH: 28
<212> TYPE: DNA
<213> ORGANISM: Artificial Sequence
<220> FEATURE:
<223> OTHER INFORMATION: primer

<400> SEQUENCE: 18
cgacagtcac aaggaaacta ctaaggta                                      28

<210> SEQ ID NO 19
<211> LENGTH: 24
<212> TYPE: DNA
<213> ORGANISM: Artificial Sequence
<220> FEATURE:
<223> OTHER INFORMATION: primer

<400> SEQUENCE: 19
aggatccaga ggatgagact gaaa                                          24

<210> SEQ ID NO 20
<211> LENGTH: 25
<212> TYPE: DNA
<213> ORGANISM: Artificial Sequence
<220> FEATURE:
<223> OTHER INFORMATION: primer

<400> SEQUENCE: 20
ccttagctga ttccactacg tacca                                         25

<210> SEQ ID NO 21
<211> LENGTH: 27
<212> TYPE: DNA
<213> ORGANISM: Artificial Sequence
<220> FEATURE:
<223> OTHER INFORMATION: primer

<400> SEQUENCE: 21
```

-continued agaagttcaa tgtttcgttt catgtaa                                       27

<210> SEQ ID NO 22
<211> LENGTH: 29
<212> TYPE: DNA
<213> ORGANISM: Artificial Sequence
<220> FEATURE:
<223> OTHER INFORMATION: primer

<400> SEQUENCE: 22
gaacggaaac atagtagaac acttattca                                     29

<210> SEQ ID NO 23
<211> LENGTH: 26
<212> TYPE: DNA
<213> ORGANISM: Artificial Sequence
<220> FEATURE:
<223> OTHER INFORMATION: primer

<400> SEQUENCE: 23
gtcgacaaat attttcctat aacata                                        26

<210> SEQ ID NO 24
<211> LENGTH: 25
<212> TYPE: DNA
<213> ORGANISM: Artificial Sequence
<220> FEATURE:
<223> OTHER INFORMATION: primer

<400> SEQUENCE: 24
ggatcctcat ctctaagata ttact                                         25

<210> SEQ ID NO 25
<211> LENGTH: 23
<212> TYPE: DNA
<213> ORGANISM: Artificial Sequence
<220> FEATURE:
<223> OTHER INFORMATION: primer

<400> SEQUENCE: 25
tctagatggt tttggaggat aga                                           23

<210> SEQ ID NO 26
<211> LENGTH: 23
<212> TYPE: DNA
<213> ORGANISM: Artificial Sequence
<220> FEATURE:
<223> OTHER INFORMATION: primer

<400> SEQUENCE: 26
ggatcccatt tcatcgattt ctt                                           23

<210> SEQ ID NO 27
<211> LENGTH: 24
<212> TYPE: DNA
<213> ORGANISM: Artificial Sequence
<220> FEATURE:
<223> OTHER INFORMATION: primer

<400> SEQUENCE: 27
ctcgagatgg ttttggagga taga                                          24

<210> SEQ ID NO 28
<211> LENGTH: 24
<212> TYPE: DNA

```
<213> ORGANISM: Artificial Sequence
<220> FEATURE:
<223> OTHER INFORMATION: priemr

<400> SEQUENCE: 28
ctcgagtcat ttcatcgatt tctt                                          24

<210> SEQ ID NO 29
<211> LENGTH: 17
<212> TYPE: DNA
<213> ORGANISM: Artificial Sequence
<220> FEATURE:
<223> OTHER INFORMATION: primer

<400> SEQUENCE: 29
aatacgactc actatag                                                  17

<210> SEQ ID NO 30
<211> LENGTH: 28
<212> TYPE: DNA
<213> ORGANISM: Artificial Sequence
<220> FEATURE:
<223> OTHER INFORMATION: primer

<400> SEQUENCE: 30
ggctactagt gcgccaacgt tgatacaa                                      28

<210> SEQ ID NO 31
<211> LENGTH: 27
<212> TYPE: DNA
<213> ORGANISM: Artificial Sequence
<220> FEATURE:
<223> OTHER INFORMATION: primer

<400> SEQUENCE: 31
cccggatccg aatggaagtg gaagaag                                       27

<210> SEQ ID NO 32
<211> LENGTH: 36
<212> TYPE: DNA
<213> ORGANISM: Artificial Sequence
<220> FEATURE:
<223> OTHER INFORMATION: primer

<400> SEQUENCE: 32
agaagttccg aggaaattgg tgacgtcatt tgccga                             36

<210> SEQ ID NO 33
<211> LENGTH: 36
<212> TYPE: DNA
<213> ORGANISM: Artificial Sequence
<220> FEATURE:
<223> OTHER INFORMATION: primer

<400> SEQUENCE: 33
tcggcaaatg acgtcaccaa tttcctcgga acttct                             36

<210> SEQ ID NO 34
<211> LENGTH: 27
<212> TYPE: DNA
<213> ORGANISM: Artificial Sequence
<220> FEATURE:
<223> OTHER INFORMATION: primer

<400> SEQUENCE: 34
cccgaattct ttagcttctt gaaccag                                       27
```

```
<210> SEQ ID NO 35
<211> LENGTH: 27
<212> TYPE: DNA
<213> ORGANISM: Artificial Sequence
<220> FEATURE:
<223> OTHER INFORMATION: primer

<400> SEQUENCE: 35
cccggatcca aaacagcctt ttacata                                        27

<210> SEQ ID NO 36
<211> LENGTH: 65
<212> TYPE: DNA
<213> ORGANISM: Artificial Sequence
<220> FEATURE:
<223> OTHER INFORMATION: primer

<400> SEQUENCE: 36
cccgaattct caagcgtaat ctggaacatc gtatgggtac cccccatgac ccattggaat    60
actcg                                                                65

<210> SEQ ID NO 37
<211> LENGTH: 65
<212> TYPE: DNA
<213> ORGANISM: Artificial Sequence
<220> FEATURE:
<223> OTHER INFORMATION: primer

<400> SEQUENCE: 37
cccgaattct taagcgtaat ctggaacatc gtatgggtac ccccgcttc ttgaaccagt     60 tgatc                                                                65

<210> SEQ ID NO 38
<211> LENGTH: 18
<212> TYPE: DNA
<213> ORGANISM: Artificial Sequence
<220> FEATURE:
<223> OTHER INFORMATION: primer

<400> SEQUENCE: 38
atcaagcttg ctctagag                                                  18

<210> SEQ ID NO 39
<211> LENGTH: 20
<212> TYPE: DNA
<213> ORGANISM: Artificial Sequence
<220> FEATURE:
<223> OTHER INFORMATION: primer

<400> SEQUENCE: 39
gggatccaga tggttttgga                                                20
```

METHOD FOR CHANGING NITROGEN UTILIZATION EFFICIENCY IN PLANTS

RELATED APPLICATIONS

This is a division of U.S. application Ser. No. 12/832,234, filed on Jul. 8, 2010, which claims benefit of U.S. Provisional Application 61/223,744, filed on Jul. 8, 2009. The contents of the prior applications are incorporated herein by reference in their entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_List_16024_00012_US_ST25.txt. The size of the text file is 39 KB, and the text file was created on Jul. 8, 2010.

FIELD OF THE INVENTION

The present invention is related to a method for changing nitrogen utilization efficiency in a plant by regulating expression of a nitrate transporter.

BACKGROUND OF THE INVENTION

Nitrogen fertilizer is one of the most expensive nutrients to supply. 50-70% of the applied nitrogen is lost from the plant-soil system and causes water pollution (Peoples, 1995, in: P. E. Bacon, Editor, *Nitrogen Fertilizer in the Environment*, Marcel Dekker, 565-606). Improving nitrogen utilization efficiency ("NUE") is important to reduce the cost of crop production as well as environmental damage. Nitrogen remobilization is one of the key steps to improve NUE (Mickelson et al., 2003, J Exp Bot 54, 801-812; Masclaux-Daubresse et al., 2008, Plant Biol (Stuttg) 10 Suppl 1, 23-36).

When plants encounter nutrient deficiency, nitrogen can be recycled from older to younger leaves to sustain the growth of developing tissues. Nitrate remobilization occurs not only from leaf to leaf during the vegetative stage, but also from leaf to seeds during the reproductive stage. High nutrient demand during reproductive stage cannot be satisfied by Nitrogen uptake, and nitrogen recycled from senescent tissue plays an important role in sustaining grain production. Although several studies showed that nitrate remobilization was important to increase grain yield and withstand nitrogen deprivation, little was known about nitrate remobilization. Thus, it is important to find out how the stored nitrate is retrieved to withstand nitrogen deficiency and to sustain high nitrogen demand in the reproductive stage, thereby to regulate the growth of nitrogen use efficiency in a plant.

BRIEF SUMMARY OF THE INVENTION

Accordingly, the invention relates to a discovery of *Arabidopsis* nitrate transporter NRT1.7 that is expressed in phloem, and is responsible for source-to-sink remobilization of nitrate. It is unexpectedly found in the present invention that the expression and activity of NRT1.7 involves nitrate remobilization from older leaves to young leaves in the plant so as to regulate plant growth.

In one aspect, the present invention provides a method for changing nitrogen utilization efficiency in a plant comprising regulating the expression of *Arabidopsis* NRT1.7 or an ortho- logue thereof, so that the nitrogen remobilization from older leaves to young leaves in the plant is regulated, and thereby the nitrogen utilization efficiency is changed. According to an embodiment of the invention, a transgenic plant is prepared by transforming a plant with a construct for a high or low level of expression of NRT1.7. In one example of the invention, a transgenic plant having an enhanced plant growth is prepared by transforming a plant with an expression construct comprising a DNA sequence encoding *Arabidopsis* NRT1.7 or an orthologue thereof in a high level of expression, thereby the transgenic plant has an improved nitrate remobilization from older leaves to young leaves in the plant and nitrogen utilization efficiency. In another example of the invention, the transgenic plant having a retarded plant growth is prepared by transforming a plant with a construct for inhibiting the expression of NRT1.7 gene or orthologue thereof, whereby the transgenic plant has decreased nitrogen utilization efficiency.

In another aspect, the present invention provides a new chimera nitrate transporter of a NRT1.1 and NRT1.2, providing a high nitrate transport efficiency, wherein the chimera nitrate transporter has the amino acid sequence of SEQ ID NO: 11. In one embodiment of the invention, a transgenic plant having enhanced nitrogen utilization efficiency by transforming a plant with the chimera nitrate transporter, whereby the transgenic plant has an enhanced growth.

According to the present invention, the nitrogen utilization efficiency in a plant is enhanced by overexpression of NRT1.7 or an enhanced expression of the NRT 1.7, whereby the nitrate remobilization from older leaves to young leaves in the plant is enhanced, and then the plant growth is improved.

The invention also provides an isolated DNA molecule encoding a chimera nitrate transporter having a amino acid sequence of SEQ ID NO:11, which was evidenced in Example 9 to provide high nitrate uptake so that it is believed that the nitrogen utilization efficiency can be enhanced. In one example of the invention, the nucleotide sequence encoding NRT 1.7 has a nucleotide sequence of SEQ ID NO: 10.

In a further yet aspect, the present invention provides a transgenic plant, which is transformed with an expression construct causing overexpression of NRT1.7 or enhancement of NRT1.7 function within the transgenic plant, whereby the transgenic plant enhances the nitrate remobilization from older leaves to young leaves in the plant, and the nitrogen utilization efficiency is improved. On the other hand, the present invention also provide a transgenic plant, which is transformed with an construct that has a defect in the gene of NRT1.7, wherein the defect results in inhibiting the expression of NRT1.7 or NRT1.7 mRNA to decrease quantity or availability of functional NRT1.7, whereby the nitrogen remobilization from older leaves to younger leaves in the transgenic plant is defective.

BRIEF DESCRIPTION OF THE DRAWINGS

The foregoing summary, as well as the following detailed description of the invention, will be better understood when read in conjunction with the appended drawings. It should be understood, however, that the invention is not limited to the precise arrangements and instrumentalities shown.

In the drawings:

FIG. 3A is SDS-PAGE showing the levels of NRT1.7 protein in older leaves; wherein the top part of the same membrane was hybridized with Bip antibodies as loading control, and the values of NRT1.7 protein levels normalized to Bip level, with the young leaves set at 1, were indicated below the blot; and the results found in three biological repeats were similar.

FIG. 3B is a diagram showing quantitative RT-PCR analysis of NRT1.7 expression; wherein the leaves were separated into distal lamina, proximal lamina, and central part, including midrib and petiole, for RNA isolation; NRT1.7 was preferentially expressed in the distal part of older leaves; the relative expression level shown here was the expression of NRT1.7 normalized to that of UBQ10; and the values are means±SE of four biological repeats; and the statistically significant differences were indicated by different letters ($p<0.01$).

FIG. 11 provides *Arabidopsis* NRT 1.7 amino acid sequences and the various orthologue and paralogues sequences with their percent homology.

DETAILED DESCRIPTION OF THE INVENTION

Figure 1:
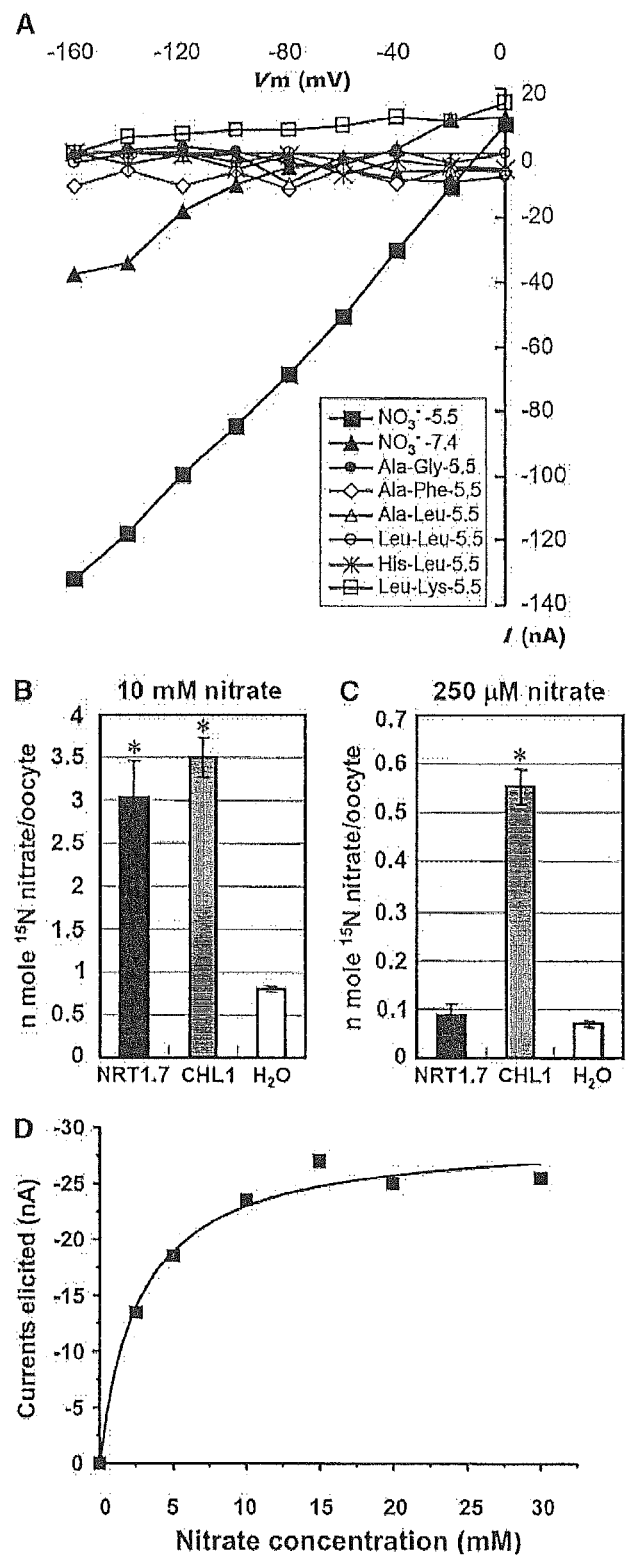
FIG. 1A is a diagram showing the voltage-clamped NRT1.7 cRNA-injected oocytes demonstrating their response to 10 mM nitrate at pH 5.5 with inward current.
FIG. 1B is a diagram showing the low-affinity nitrate uptake activity of NRT1.7-, CHL1-(NRT1.1) or water-injected oocytes, wherein the values are means SD (n=5)
FIG. 1C is a diagram showing the high-affinity nitrate uptake activity of NRT1.7-, CHL1- or water-injected oocytes, wherein values are means±SD (n=10, 9, 6 for NRT1.7-, CHL1- or water-injected oocytes, respectively)
FIG. 1D is a diagram showing kinetics of nitrate-elicited currents in a single NRT1.7 cRNA-injected oocyte determined by measuring inward current elicited by different concentrations of nitrate at pH 5.5 and plotting as a function of the external nitrate concentration; which is representative of the results from six oocytes from four different frogs.

In the present invention, it is unexpectedly found that the *Arabidopsis thaliana* nitrate transporter NRT1.7 provides new insights into nitrate remobilization. Accordingly, the present invention provides a method for changing nitrogen utilization efficiency in a plant comprising regulating the expression of *Arabidopsis* NRT1.7 or an orthologue thereof, so that the nitrogen remobilization from older leaves to young leaves in the plant is regulated, and thereby the nitrogen utilization efficiency is changed.

The term "*Arabidopsis* NRT1.7" or "NRT1.7" as used herein refers to *Arabidopsis* nitrate transporter NRT1.7, having the amino acid sequence of SEQ ID NO:2, or a protein encoded by a nucleic acid sequence of SEQ ID NO:1.

The term "orthologue" used herein refers to one of two or more homologous gene sequences found in different species. In the invention, the orthologue of *Arabidopsis thaliana* nitrate transporter NRT1.7 includes but not limited to any transporter having an amino acid sequence that is at least 40% homologous to the consensus amino acid sequence of NRT1.7 (such as the transporter having the amino acid sequence of SEQ ID NO: 2), preferably at least 60%, most preferably 80% homologous to the consensus amino acid sequence of NRT1.7, such as those shown in FIG. 11.

According to an embodiment of the invention, a transgenic plant is prepared by transforming a plant with an expression construct for a high or low level of expression of NRT1.7. In one example of the invention, a transgenic plant having an enhanced plant growth is prepared by transforming a plant with an expression construct comprising a DNA sequence encoding *Arabidopsis* NRT1.7 or an orthologue thereof in a high level of expression, thereby the transgenic plant has an improved nitrate remobilization and nitrogen utilization efficiency. In another example of the invention, the transgenic plant having a retarded plant growth is prepared by transforming a plant with an expression construct comprising null mutation of the NRT1.7 gene, whereby the transgenic plant has a decreased nitrogen utilization efficiency.

Based on the several quantitative trait locus analyses as obtained, the grain yield and nitrogen utilization efficiency were well correlated with nitrate storage capacity and efficient remobilization. Western blotting, quantitative RT-PCR, and □-glucuronidase reporter analysis as obtained in the present invention indicated that NRT1.7 was expressed in the phloem of the leaf. In nrt1.7 mutants, more nitrate was present in the older leaves, less $^{15}NO_3-$ spotted on old leaves was remobilized into N-demanding tissues, and less nitrate was detected in the phloem exudates of old leaves. Meanwhile, nrt1.7 mutants also showed growth retardation when external nitrogen was depleted. It is concluded that nitrate remobilization is important to sustain vigorous growth during nitrogen deficiency, and the nitrogen utilization efficiency can be changed by regulating the expression of NRT1.7 in a plant.

According to the present invention, a method of enhancing nitrogen utilization efficiency in a plant comprises overexpressing NRT1.7 or enhancing NRT1.7 function in a plant, wherein the nitrogen remobilization from older leaves to young leaves in the plant is enhanced, thereby the nitrogen utilization efficiency is improved.

In the invention, NRT1.7 gene expression is regulated to produce more NRT1.7 protein than ordinary conditions in the corresponding wild type plants. Methods for overexpression of a protein in vivo are well known in the art. Thus the invention also encompasses all possible methodology for overexpression NRT1.7 gene or modulating activity of NRT1.7 protein in a plant, including regulation of transcription and post-translation regulation. For example, the modulating of gene expression may be used, i.e. by modulating the expression of the gene itself by a suitable promoter and/or a transcription enhancer or a translation enhancer. Alternatively, the modulation of expression as mentioned above is effected in an indirect way, for example as a result of increased levels and/or activity of factors that control the expression of NRT1.7 gene. In one example of the invention, the enhancer may be used to enhance transcription levels of genes in a gene cluster.

According to the invention, any enhancer for enhancing the expression of NRT1.7 may be used to prepare an expression construct for transforming a plant to produce a transgenic plant. For example, CaMV 35S enhancers (Weigel et al., Plant Physiol. 122(4):1003-1013. 2000, April) may be used for enhancing the expression of NRT1.7. In one example of the present invention, 35S enhancer (SEQ ID NO:4) can be modified to link with NRT1.7 promoter (SEQ ID NO:3) or inserted into downstream of NRT1.7 coding region alone. In one embodiment of the invention, 35S enhancer is operatedly linked with NRT1.7 promoter to produce an artificial nucleic acid sequence of SEQ ID NO: 5. One can prepare an expression construct comprising the chimera DNA sequence of SEQ ID NO: 5, inserted to an expression construct to overexpress NRT1.7.

According to the invention, if a transgenic plant has the overexpression of NRT1.7 or enhancing the activity of NRT1.7, the nitrogen remobilization from older leaves to younger leaves in the transgenic plant will be enhanced; and accordingly it is believed that the transgenic plant has faster growth and higher yield. Therefore, the present invention provides a transgenic plant transformed with an expression construct comprising a nucleic acid sequence causing a high level of expression, such as overexpression, of NRT1.7 or enhancement of NRT1.7 function within the transgenic plant, wherein expression of the DNA molecule in the transgenic plant enhances the nitrogen remobilization from older leaves to young leaves in the plant, thereby the nitrogen utilization efficiency is improved.

The phrase/clause "faster growth" or "the growth is enhanced" used herein refers to the increase either in weight or size, for example fresh weight, or in biomass per time unit is greater that that of the plant of same species.

The term "yield" used herein refers to the amount of harvested material per area of production. The term "higher yield" means an increase in biomass in one or more parts of a plant relative to that of corresponding wild type plants. The harvested parts of the plant can be such as seed (e.g. rice, sorghum or corn), root (e.g. sugar beet), fruit (e.g. apple), flowers, or any other part of the plant, which is of economic value.

Transformation of a plant species is now fairly routine technique. Advantageously, any of several transformation methods may be used to introduce the gene of interest into a suitable ancestor cell. Transformation methods include, but not limited to, the use of liposomes, electroporation, chemicals that increase free DNA uptake, injection of the DNA directly into the plant, particle gun bombardment, viruses or pollen and microinjection. In one embodiment of the present invention, plant transformation was performed as described in Clough et al, 1998, Plant J 16, 735-743.

It is found in the present invention that NRT1.7 involves in nitrate remobilization from the old leaves to young leaves in a plant. In one example of the present invention, a mutant of nrt1.7 defective in this process was prepared to retard the plant growth when the plants encountered long-term severe nitrogen deficiency during vegetative growth. It was indicated that internal nitrate remobilization between leaves was important for plants to cope with nitrogen deficiency and the importance of enhanced nitrogen use efficiency for maximum growth. The present invention further provides a method for retarding growth in a plant comprising decreasing quantity or activity of NRT1.7, or inhibiting the expression of a gene encoding NRT1.7 within the plant, thereby causes the defect in remobilizing nitrogen from older leaves to younger leaves so as to retard growth in the plant.

Techniques for decreasing quantity or activity of a protein, or inhibiting the expression of a gene in vivo are also well known and envisaged in the art, whether by a direct or indirect approach. Examples of decreasing expression includes, but not limited, by anti-sense techniques, co-suppression techniques, RNAi techniques, small interference RNAs (siRNAs), micorRNA (miRNA), the use of ribozymes, etc. According to one embodiment of the present invention, the growth of a plant was modified by introducing into a plant an additional copy (in full or in part) of a NRT1.7 gene fragment already present in a host plant. The additional gene silences the endogenous gene, giving rise to a phenomenon known as co-suppression. In another embodiment of the present invention, gene silencing may also be achieved by insertion mutagenesis, e.g., T-DNA insertion or transposon insertion, or by gene silencing strategies as described in published prior arts.

The present invention also provides a transgenic plant obtainable by the methods for decreasing quantity or activity of a protein, or inhibiting the expression of a gene in vivo above. In one example of the invention, the transgenic plant had defects in the gene of NRT1.7, wherein the defects in the gene resulted in inhibiting the expression of NRT1.7 mRNA or proteins to decrease quantity or availability of functional NRT1.7, thereby the nitrogen remobilization from older leaves to younger leaves in the transgenic plant is defective. According to the invention, such transgenic plant performs growth retardation during nitrogen starvation.

The present invention provides a new chimera nitrate transporter having the amino acid sequence of SEQ ID NO: 11, and the DNA molecule having the sequence coding for this chimera protein. In one example of the invention, an isolated DNA molecule encoding a chimera nitrate transporter named as NC4N is provided, which comprises the nucleotide sequence of SEQ ID NO:10, coding for the chimera nitrate transporter having the amino acid sequence of SEQ ID NO: 11. According to the invention, the chimera protein is prepared from NRT1.1 and NRT1.2 with NRT1.2-NRT1.1-NRT1.2 shuffling form, in which at the residues of 76-195 positions of NRT1.2 amino acid sequences (SEQ ID NO: 9) was replaced by at the residues of 78-200 positions of NRT1.1 amino acid sequences (SEQ ID NO: 7).

*Arabidopsis* NRT1.1 and NRT1.2 participate in nitrate uptake using a proton gradient as a driving force to transport nitrate from the soil into plant cells. Unexpectedly, the inventors found that the chimera protein performed better activity on nitrate uptake than wild type NRT1.1 and NRT1.2. In one embodiment of the invention, functional Analysis of the chimera protein was determined by *Xenopus laevis* oocytes test as described in the Example 9. As evidenced in FIG. 10, both NRT1.1 cRNA-injected oocytes and NC4N cRNA-injected oocytes were found to take up more nitrate than water-injected oocytes. Moreover, NC4N cRNA-injected oocytes were found to take up more nitrates than NRT1.1 cRNA-injected oocytes. The results indicate that the chimera fused protein of the present invention has better transport activity than any known NRT transports.

Furthermore, the present invention provides a method enhancing nitrogen utilization efficiency in a plant comprising transforming a plant with the DNA molecule encoding the claimed chimera transporter having the amino acid sequence of SEQ ID NO: 11 to produce a transgenic plant, wherein the nitrogen utilization efficiency is enhanced in the transgenic plant, and subsequently, the transgenic plant has faster growth and higher yield. Preferably, the DNA molecule encoding the claimed chimera transporter is driven by a NRT1.7 promoter in the transgenic plant.

The present invention is further illustrated by the following examples, which are provided for the purpose of demonstration rather than limitation.

EXAMPLES

Methods and Materials

Functional Analysis of NRT1.7 in *Xenopus laevis* Oocytes

A full length cDNA fragment of NRT1.7 (SEQ ID NO:1) was cloned into the pGEMHE vector (Liman et al., 1992, Neuron 9, 861-871) to generate pGEMHE-NRT1.7. The pGEMHE-NRT1.7 was linearized using NheI, and capped mRNA was transcribed in vitro using mMESSAGE mMACHINE kits (Ambion). Oocytes were injected with 100 ng of NRT1.7 cRNA as described previously (Tsay et al., 1993, Cell 72, 705-713). Electrophysiological analyses of injected oocytes were performed as described previously (Huang et al., 1999, Plant Cell 11, 1381-1392). Nitrate uptake assays using $^{15}$N-nitrate were performed as described previously using a continuous-flow isotope ratio mass spectrometer coupled with a carbon nitrogen elemental analyzer (ANCA-GSL MS; PDZ Europa; (Lin et al., 2008, Plant Cell 20, 2514-2528)), and oocytes injected with CHL1 cRNA (Liu et al., 1999, Plant Cell 11, 865-874) were used as a positive control.

Plant Growth Condition and nrt1.7 Mutants

Unless otherwise indicated, most *Arabidopsis thaliana* plants used in this study were grown in soil containing compost:humus at 3:1, at 22° C., with 16-hr photoperiod, and 60% relative humidity, and irrigated with HYPONeX #2 fertilizer at final concentrations of 6 mM nitrate, 5.3 mM potassium, and 3.5 mM phosphate. For nitrogen starvation experiments, plants were grown in soil containing perlite:vermiculite at 1:2 and covered with a thin layer of fine vermiculite, irrigated with HYPONeX #2 fertilizer for 10 or 25 days as indicated in the figure legends, and then watered with a nitrogen-depleted solution containing 5 mM $K_2HPO_4/KH_2PO_4$, pH 5.5, and the basal nutrients (1 mM $MgSO_4$, 0.1 mM $FeSO_4$-EDTA, 0.5 mM $CaCl_2$, 50 μM $H_3BO_3$, 12 μM $MnSO_4$, 1 μM $ZnCl_2$, 1 μM $CuSO_4.5H_2O$, and 0.2 μM $Na_2MoO_4.2H_2O$). For phloem exudates collection and measurement of NRT1.7 expression in response to starvation, plants were grown hydroponically in a solution containing 1 μM $K_2HPO_4/KH_2PO_4$ at pH 5.5, the basal nutrients described above and with or without 1 mM $NH_4NO_3$. All experiments compared wild-type and mutant plants grown in the same pot.

The nrt1.7-1 was obtained from the ALPHA population (WS ecotype) of T-DNA-tagged plants generated by the *Arabidopsis* Knockout Facility at the University of Wisconsin Biotech Center (Krysan et al., 1999, Plant Cell 11, 2283-2290). The primers used for PCR screening were JL202 (Lin et al., 2008, Plant Cell 20, 2514-2528) and the NRT1.7 forward primer (SEQ ID NO:12: 5'-CCACACCCACCATATAT-TATCTACTCACT-3'). The second mutant nrt1.7-2 (SALK 053264) was provided by the Salk Institute Genomic Analysis Laboratory (Alonso et al., 2003, Science 301, 653-657).

Antibody and Western Blot

The anti-NRT1.7 rabbit polyclonal antibody was generated using a peptide corresponding to the first N-terminal 50 amino acids. The cDNA fragment encoding the N-terminal 1-50 a.a. was amplified by PCR using primers pair of (SEQ ID NO:13: forward 5'-gaattctaATGGTTTTGGAGGATAG-3' and SEQ ID NO:14: reverse 5'-aaGCTTTTTCTCTACCTTCTCAG-3'), which introduced EcoRI and HindIII restriction sites respectively, and subcloned into pGEX-KG in frame with the GST to generate pGEX-KG-NRT1.7-N50. GST-fusion protein was isolated from *E. coli* (BL21) transformant and purified by GST-beads. Purified GST-fusion protein was emulsified with Freund's adjuvant and injected into New Zealand rabbits according to the protocol of Spindler et al. (Spindler et al., 1984, J Virol 49, 132-141).

For protein gel blot analysis, tissues were homogenized in ice cold extraction buffer consisting of 15 mM Tris-HCl, pH 7.8, 250 mM sucrose, 1 mM EDTA, 2 mM DTT, 1 mM phenylmethylsulfonyl fluoride, 0.6% polyvinylpyrrolidone, and protease inhibitor cocktail (Roche). The homogenate was then centrifuged at 10,000×g for 10 min and the supernatant was collected into a chilled tube. The supernatant was centrifuged at 100,000×g for 1 h, and then the pellet, the microsomal fraction, was dissolved in 4% SDS. 10 micrograms of protein were analyzed by SDS-PAGE. Detections were performed using the ECL protein gel blotting system (Amersham, GE Healthcare, UK). Anti-NRT1.7, Anti-BiP and horseradish peroxidase-labeled anti-rabbit IgG antibody were used at dilutions of 1:2000, 1:2000 and 1:10000, respectively.

RT-PCR and Quantitative RT-PCR

The ImProm-II reverse transcriptase (Promega), oligo(dT) primers, and the RNA isolated from different developmental stages of leaves and flowers were used to synthesize the first-strand cDNAs. Primers across the intron of Histone were used to exclude genomic contamination. Primers specific for the NRT1.7, NIA2 and UBQ10 gene were designed by ABI software. Quantitative PCR was performed in AB7500 using Power SYBR Green (ABI System). The primers used were as follows:

TABLE 1

Primer Sequence

| Gene | Sequence | SEQ ID NO: |
|---|---|---|
| Histone (Forward) | 5'-AACCACTGGAGGAGTCAAGA-3' | 15 |
| Histone (Reverse) | 5'-CAATTAAGCACGTTCTCCTCT-3' | 16 |
| NRT1.7 (Forward) | 5'-CAACAGTCAGTTTCCAGAGCACAT-3' | 17 |
| NRT1.7 (Reverse) | 5'-CGACAGTCACAAGGAAACTACTAAGGTA-3' | 18 |
| NIA2 (Forward) | 5'-AGGATCCAGAGGATGAGACTGAAA-3' | 19 |
| NIA2 (Reverse) | 5'-CCTTAGCTGATTCCACTACGTACCA-3' | 20 |
| UBQ10 (Forward) | 5'-AGAAGTTCAATGTTTCGTTTCATGTAA-3' | 21 |
| UBQ10 (Reverse) | 5'-GAACGGAAACATAGTAGAACACTTATTCA-3 | 22 |

Promoter-GUS Analysis

A 1.35-kb genomic fragment of NRT1.7 promoter (−1346 to +3 bp) was generated by PCR using the primers forward 5'-gtcgaCAAATATTTTCCTATAACATA-3' (SEQ ID NO: 23:) and reverse 5'-ggatccCATCTCTAAGATATTACT-3' (SEQ ID NO: 24), cut with XbaI and BamHI, and then inserted in-frame in front of uidA (GUS) of pBI101. Plant transformation was performed as described (Clough et al, 1998, Plant J 16, 735-743). Homozygous transgenic plants (T3) 28-32 days old cultivated in soil with full nutrient were used for GUS histochemical assay, with GUS staining as described previously (Lagarde et al., 1996, The Plant Journal 9, 195-203). Cross-sections of 2 µm thickness were prepared using a microtome (Ultracut E, Reichert-Jung) from tissues embedded in LR white.

Whole-Mount Immunolocalization

To enhance the specificity, anti-NRT1.7 antiserum was affinity purified first by the antigen used to raise antiserum (a GST fusion of the first 50 amino acids of NRT1.7) and then by HA-tagged full-length NRT1.7 protein. Older (40 d old) Col and nrt1.7-2 leaves were used for whole mount immunohybridization. For antigen retrieval before hybridization, tissues were incubated in 1 mM EDTA at 95° for 5 mM and then blocked for 2 hours in blocking buffer (50 mM Tris-HCL, pH 7.5, 150 mM NaCl, and 1% gelatin). After 36 hours incubation with affinity-purified anti-NRT1.7 antiserum in 1:10 dilution at 4°, tissues were washed three times with blocking buffer and then hybridized with Alexa Fluor 488 goat anti-rabbit IgG (Molecular Probes) in 1:500 dilution. Green fluorescence was detected by a Zeiss LSM META-510 microscope with excitation at 488 nm. Fluorescence emission signals were detected using a band-pass filter of 505 to 530 nm Sieve plates were stained with 0.2% aniline blue (Water Blue; Fluka) in 50 mM Na—$PO_4$ buffer for 30 min. Aniline blue fluorescence was detected with an excitation light of 405 nm and band-pass filter of 420 to 480 nm.

GFP Fusion and Subcellular Localization

To construct the plasmid encoding NRT1.7-GFP fusion protein, NRT1.7 cDNA was amplified by PCR using the primers NRT1.7NF (SEQ ID NO:25: 5'-tctagATGGTTTTGGAGGATAGA-3') and NRT1.7NR (SEQ ID NO:26: 5'-ggatccCATTTCATCGATTTCTT-3'); the former primer introduces a XbaI restriction site and the latter removes the stop codon and introduces a BamHI restriction site. The amplified DNA fragment was then cloned in frame in front of the GFP coding region in the vector 326-GFP, leading to the final pNRT1.7-GFP construct under the control of the 35S promoter. The fusion linker between NRT1.7 and GFP contained seven amino acids (YIQGDIT). To construct the plasmid encoding pGFP-NRT1.7 fusion protein, the NRT1.7 cDNA was amplified by PCR with primers NRT1.7CF (SEQ ID NO:27: 5'-ctcgagATGGTTTTGGAGGATAGA-3' and NRT1.7CR (SEQ ID NO:28: 5'-ctcgagTCATTTCATCGATTTCTT-3') which introduced XhoI restriction sites, then cloned in frame into vector 326-GFP-nt (no termination codon) behind the GFP. The fusion linker between GFP and NRT1.7 contained thirteen amino acids (PRAIKLIDTVDLE). The vector 326-GFP was used as a free GFP control.

Transient transformation of *Arabidopsis* protoplasts with polyethylene glycol was performed as described (Yoo et al., 2007, Nat Protoc 2, 1565-1572). After transformation, protoplasts were incubated overnight at room temperature under illumination (25 µE), and then observed by a Zeiss LSM510 microscope with excitation at 488 nm, Fluorescence emission signals were detected using a band-pass filter of 500 to 530 inn for GFP and a long-pass filter of 650 nm for the far-red autoflourescence of the chloroplast.

Measurement of the Nitrate Content in *Arabidopsis* Leaves

The rosette leaves were collected and immediately frozen in liquid nitrogen. To extract nitrate, samples were boiled in water (100 µl/mg FW) and then freeze-thawed once. After filtering through 0.2 µm PVDF membrane (Pall Corporation), nitrate content of the samples was determined by HPLC using a PARTISIL 10 SAX (strong anion exchanger) column (Whatman) and 50 mM phosphate buffer, pH 3.0, as the mobile phase.

$^{15}N$ Nitrate Tracing Assay

Three days after bolting, 10 µl of 50 mM $K^{15}NO_3$ with a 98% atom excess of $^{15}N$ was spotted on distal parts of the oldest leaf About 20 hr after spotting, individual leaves and flowers were collected and dried at 80° C. for 24 hr., at which point $^{15}N$ contents were analyzed as described above.

Collection and Analysis of Phloem Exudates

Three days after bolting, phloem exudates were collected from excised leaves using procedures modified from the protocol described by Deeken et al. (Deeken et al., 2008, Plant J 55, 746-759). The third and fourth leaves were cut and the tip of the petiole was re-cut in EDTA buffer (5 mM $Na_2EDTA$, pH 7.5, osmotically adjusted to 270 mOsmol with sorbitol)

with fresh razor blades without wounding. The leaves were washed with a large volume of sterile EDTA buffer to remove contaminants and then placed in 200 µl new EDTA buffer. During phloem sap exudation, the leaves were illuminated (25 µE) and incubated in $CO_2$— and $H_2O$-saturated air. After 1 h of bleeding, the buffer solution containing phloem exudates were analyzed for nitrate and sugar content. Nitrate contents were measured by HPLC as described above. Sucrose and glucose content were measured by the DNS method as described elsewhere (Bernfeld, 1995, Methods Enzymol, 1, 149-158).

Construction of Chimera NRT Protein by Fusing NRT1.1 and NRT1.1 pGEMHE-05N was made by replacing 1-701 nucleotides of AtNRT1.2 (SEQ ID NO: 8) with AtNRT1.1 (SEQ ID NO:6). The shuffling region was generated by PCR using pGEMHE-AtNRT1.1 as template and T7 (AATACGACT-CACTATAG) (SEQ ID NO: 29) and primer1 (GGCT ACTAGTGCGCCAACGTTGATACAA) (SEQ ID NO: 30) as primer set and digestion by BamHI and SpeI.

pGEMHE-NC4N was made by replacing 1-231 nucleotides of pGEMHE-CSN with AtNRT1.2. The N-terminal region of pGEMHE-NC4N was generated by $1^{st}$ PCR, using pGEMHE-AtNRT1.2 as the template and primer2 (CCCG-GATCCGAAfGGAAGTGGAAGAAG) (SEQ ID NO: 31) and primer3 (AGAAGTTCCGAGGAAATTGGTGACGT-CATTTGCCGA) (SEQ ID NO: 32) as the primer set. The C-terminal region of pGEMHE-NC4N was made by $2^{nd}$ PCR with pGEMHE-05N as template, and primer4 (TCG-GCAAATGACGTC ACCAATTTCCTCGGAACTTCT) (SEQ ID NO: 33) and primer 5 (CCCGAATTCTTTAGCT-TCTTGAACCAG) (SEQ ID NO: 34) as the primer set. The $3^{rd}$ PCR of pGEMHE-NC4N construction was done by using the product of $1^{st}$ and $2^{nd}$ PCR products as the template and primer2 and primer 5 as the primer set. The chimeric fragment (SEQ ID NO: 10) was digested by BamHI and EcoRI and then ligated into pGEMHE vector to obtain pGEMHE-NC4N.

In order to make the pGEMHE constructs with HA tag, the AtNRT1.1-HA fragment was done by PCR with pGEMHE-AtNRT1.1 as the template, primer6 (CCCGGATCCAAAA-CAGCCTTTTACATA) (SEQ ID NO: 35) and primer 7 (CCCGAATTCTCAAGCGTAATCTGGAA-CATCGTATGGGTACCCCCCATGACCCA TTG-GAATACTCG) (SEQ ID NO: 36) as primer set; NC4N-HA was done by PCR with pGEMHE-NC4N as the template primer2 and primer8 (CCCGAATTCTTAAGCGTAATCTG-GAACATCGTATGGGTACCCCCCGCTTCTTG AAC-CAGTTGATC) (SEQ ID NO: 37) as the primer set. The fragments with HA tag were digested by BamHI and EcoRI and then ligated into pGEMHE vector.

The final NC4N chimera protein has 588 amino acids represented by SEQ ID NO:11 with NRT1.2-NRT1.1-NRT1.2 shuffling form, in which at the residues of 76-195 positions of NRT1.2 amino acid sequences (SEQ ID NO: 9) was replaced by at the residues of 78-200 positions of NRT1.1 amino acid sequences (SEQ ID NO: 7).

Accession Numbers

Sequence data enclosed herein can be found in the GeneBank/EMBL data libraries under the following accession numbers: At1g69870 (NRT1.7), At1g12110 (CHL1, NRT1.1), At1g69850 (NRT1.2), At3g21670 (NTP3, NRT1.3), At2g26690 (NTP2, NRT1.4), At1g32450 (NRT1.5), At1g27080 (NRT1.6), At1g08090 (NRT2.1), At1g08100 (NRT2.2), At1g12940 (NRT2.7), At3g45650 (NAXT1), At3g54140 (PTR1), At2g02040 (PTR2), At5g46050 (PTR3), At5g40890 (CLCa), At5g40780 (LHT1), At4g05320 (UBQ10), At1g22710 (SUC2), At4g22200 (AKT2), At4g40040 (Histone), and At5g42020 (BiP).

Example 1

NRT1.7 Encodes a Low Affinity Nitrate Transporter

In *Arabidopsis*, there are 53 NRT1 (PTR) genes, some of which are known to transport nitrate, while others transport dipeptides. To determine the substrate specificity of NRT1.7, in vitro-synthesized cRNA was injected into *Xenopus* oocytes for electrophysiological analysis. After 2-day incubation in ND96, oocytes were voltage clamped at −60 mV, and then subjected to 300 ms voltage pulses from 0160 mV in −20 mV increments. NRT1.7-injected oocytes responded to 10 mM nitrate at pH 5.5 with inward currents. And the inward currents were elicited by nitrate but not by the dipeptides tested (FIG. 1A). The current elicited by nitrate was pH-dependent, with little or no current detected when exposed to nitrate at pH7.4. The pH dependence of the nitrate elicited currents suggested that NRT1.7 is a proton-coupled nitrate transporter.

Most of the nitrate transporters in NRT1 (PTR1) family function as a low-affinity transporter with exception of NRT1.1 (CRL1), which is a dual-affinity nitrate transporter. To determine the affinity of NRT1.7, the high- and low-affinity nitrate transport activities of cRNA-injected oocytes were assessed by incubating the oocytes with 10 mM $^{15}$N-nitrate for 2 hours or 250 µM $^{15}$N-nitrate for 1 hour, respectively. Consistent with the previous data, CRL1 cRNA-injected oocytes showed both high- and low-affinity nitrate transport, while NRT1.7 cRNA-injected oocytes were found to take up nitrate only with low affinity (FIGS. 1B and 1C), The $K_m$ of NRT1.7 for nitrate was calculated from currents elicited at −60 mV by different concentrations of nitrate. The average $K_m$ calculated from 6 independent oocytes was 2.7±0.6 mM (FIG. 1D).

Example 2

NRT1.7 is Expressed in Phloem Tissue of Old Leaves

Figure 2:
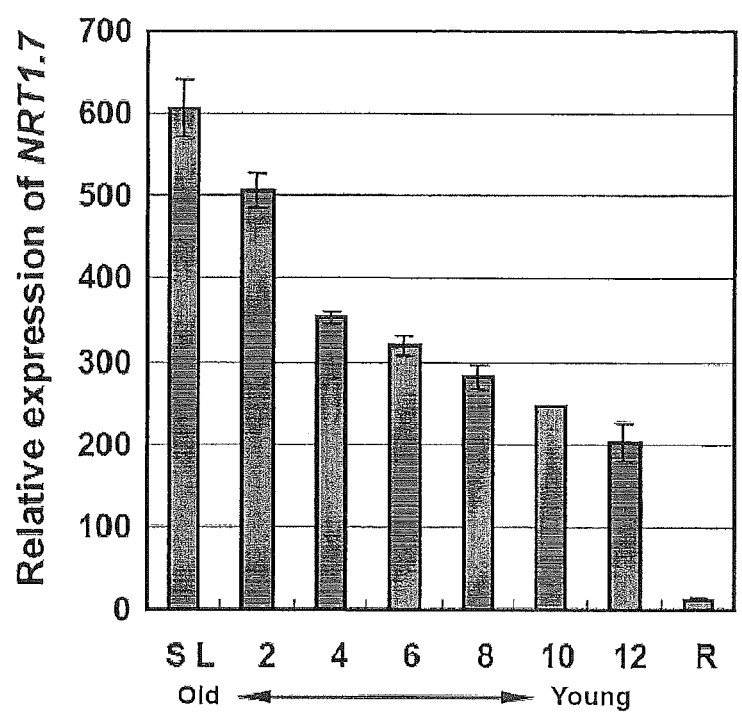
FIG. 2 is a diagram showing nrt1.7 expression level in vegetative tissues; wherein the number indicated rosette leaves order, and senescence leaf (S L) is 35 days old, rosette leaves and root were 17 days old grown on soil under continuous light at 23° and 65% relative humidity; nrt1.7 expression level was high in older leaves and very low in root.
Figure 3:
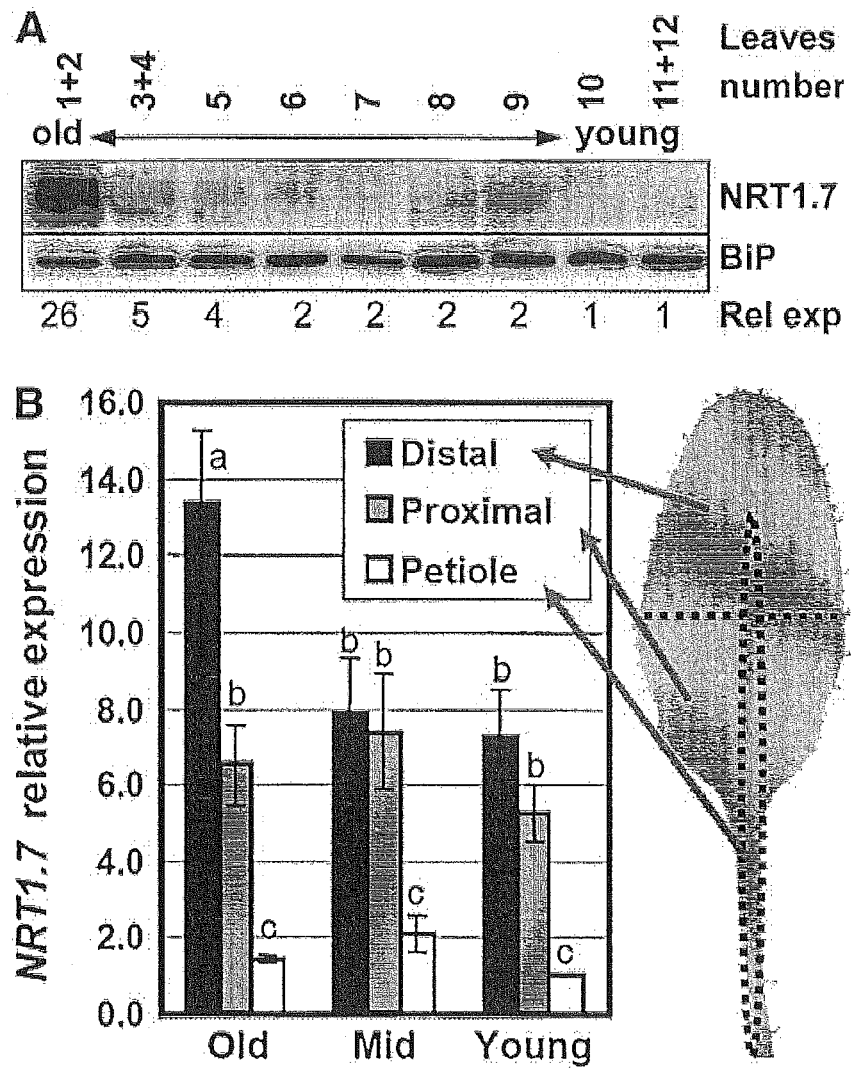

Microarray data from the public resource *A. thaliana* Expression Database CSB.DB shows that little or no expression of NRT1.7 can be detected in root, and that transcription levels in leaves increased as leaves age (FIG. 2). The differential expression of NRT1.7 in old and young leaves was further confirmed here by Western Blot analysis (FIG. 3A). Using BiP as loading control, the NRT1.7 protein level in the oldest leaves was about 25 times higher than that in the youngest leaves. In addition, the leaves were separated into distal lamina, proximal lamina, and central part including midrib and petiole for quantitative RT-PCR analysis. The NRT1.7 mRNA level was higher in the distal lamina of older leaves (FIG. 3B).

To determine where NRT1.7 is expressed, 13 independent transgenic lines expressing GUS driven by NRT1.7 promoter were analyzed. Consistent with Western Blot result, GUS staining was stronger in the older leaves, while no staining was detected in the younger leaves. In between, there were a few transition leaves with GUS staining extending from the tip to the base of the leaves (indicated by arrows in FIG. 4A). A similar pattern was found in all of the 13 independent lines. This expression pattern of NRT1.7 suggested that it might be involved in phloem loading, particularly in matured leaves.

Figure 4:
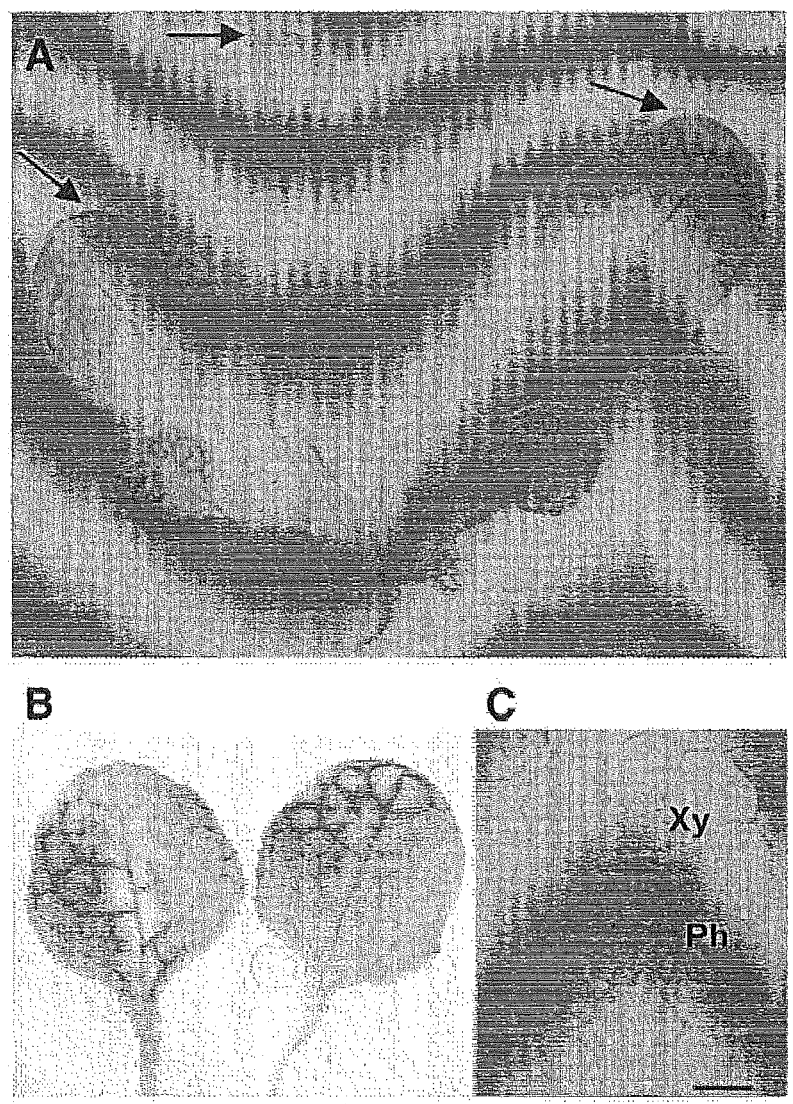
FIG. 4 are images showing (A) histochemical localization of GUS activity in 28 days old pNRT1.7-GUS plants; (B) GUS activity in minor vein of a 32 days old pNRT1.7-GUS plants; (C) cross section of minor veins of a pNRT1.7-GUS plants; wherein GUS activity was located at the sieve element and companion cell complex (Xy means xylem, Ph means phloem).

Closer examination of the GUS staining indicated that NRT1.7 was mainly expressed in minor veins (FIG. 4B). In addition, microscopic analysis of the leaf sections indicated that the expression was restricted to the sieve element and companion cell complex (FIG. 4C).

Example 3

NRT1.7 is Localized to the Plasma Membrane

Figure 5:
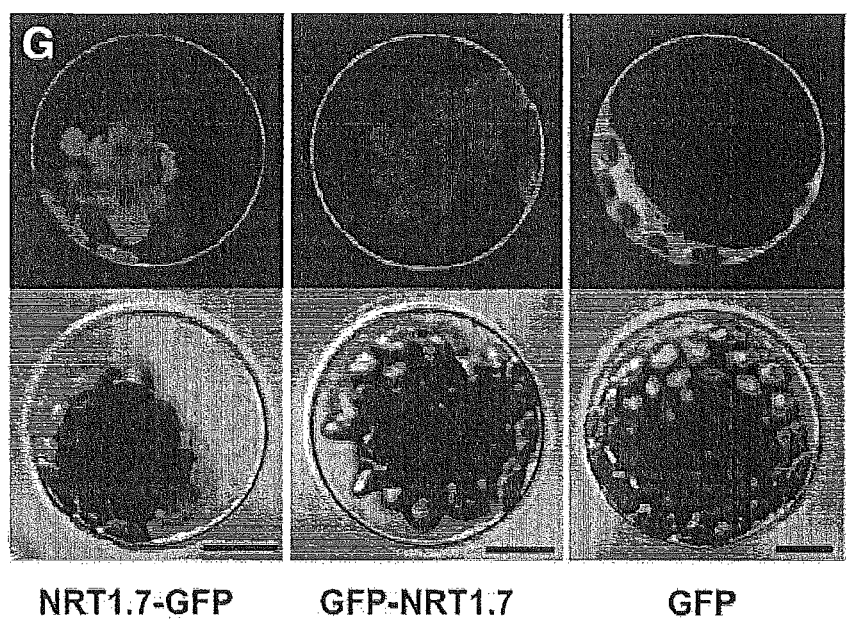
FIG. 5 is an image showing subcellular localization of NRT1.7 and GFP fusion protein in *Arabidopsis* protoplasts, wherein confocal laser scanning microscopy pictures (top panels) and corresponding bright-field images (bottom panels) of *Arabidopsis* protoplasts transiently expressing NRT1.7-GFP, GFP-NRT1.7, or GFP alone (Bar=10 μm).

To investigate the subcellular localization of NRT1.7, green fluorescent protein (GFP) fused either N-terminally or C-terminally to NRT1.7 was transiently expressed in *Arabidopsis* protoplasts under the control of the cauliflower mosaic virus 35S promoter. Green fluorescence was seen in cytoplasm in the GFP control, while the green fluorescence of NRT1.7-GFP and GFP-NRT1.7 (FIG. 5) was detected as a fine ring at the cell periphery, external to the chloroplasts, indicating that NRT1.7 is localized in the plasma membrane.

Example 4

Expression of NRT1.7 is Diurnally Regulated and Temporally Opposite to that of NIA2

Figure 6:
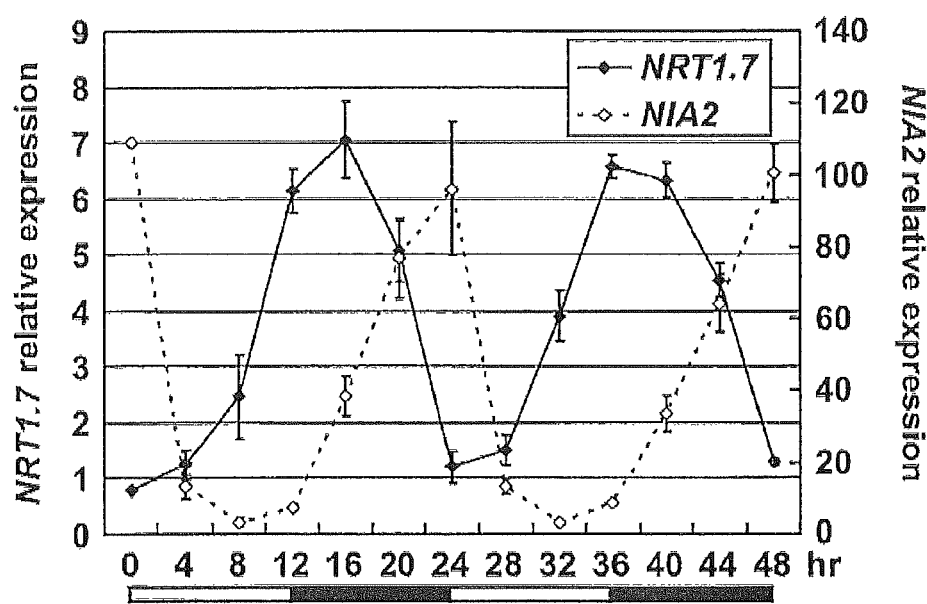
FIG. 6 is a diagram showing RNA expression levels of 20 days old wild-type (Col) plants grown under 12/12 day/night photoperiod; wherein the relative expression levels were the expression of NRT1.7 and NIA2 normalized to the expression of UBQ10; and the values were means±SE of five biological repeats at each time point except time 0 with only two biological repeats.

Shoot of plants grown under 12/12 day/night cycle for 20 days were collected to determine the diurnal changes in the expression of NRT1.7 and nitrate reductase gene NIA2. Q-PCR analysis indicated that the NRT1.7 transcript level increased gradually during the light period, reached a maximum in the early part of the dark period, and declined thereafter (FIG. 6). In contrast, NIA2 transcript levels decreased during light period, were minimal at the late stage of the light period, and then increased gradually during the dark period. This opposite temporal pattern of NRT1.7 and NIA2 mRNA levels suggests that NRT1.7 is needed when NR activity is low.

Example 5 nrt1.7 Null Mutants Accumulate Higher Amount Nitrate in Older Leaf

Figure 7:
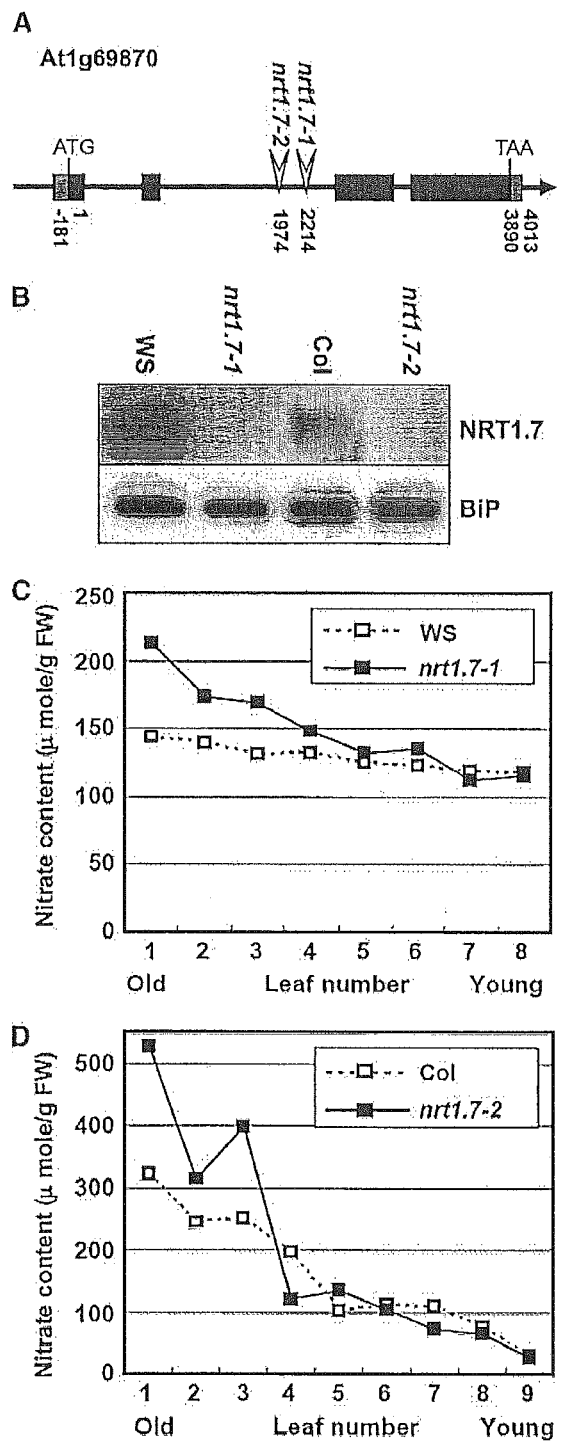
FIG. 7A provides a schematic map of the nrt1.7-1 and nrt1.7-2 mutants; wherein both mutants carried the T-DNA insertion in the second intron of the NRT1.7 gene; and the black and white boxes represented the coding and untranslated regions, respectively; wherein the number indicated the insertion site of two mutants with start codon as 1 and stop codon as 3890.
FIG. 7B provides the result of a western blot analysis of NRT1.7 protein levels in the wild-type and in homozygous nrt1.7 mutants.
FIG. 7C and FIG. 7D are diagrams showing the nitrate contents accumulated in old leaves of mutants; wherein the similar results were observed in three different pairs of Ws and nrt1.7-1 comparisons and three of Col and nrt1.7-2.

To determine the in vivo function of nrt1.7, two T-DNA insertion mutants were isolated. Mutant nrt1.7-1 in the Wassilewskija (WS) ecotype was isolated by PCR-based screening (Krysan et al., 1999, Plant Cell 11, 2283-2290), and a second mutant nrt1.7-2, SALK_053264, in the Columbia (Col) ecotype was obtained from ABRC (Alonso et al., 2003, Science 301, 653-657). In nrt1.7-1 and nrt1.7-2 mutants, one copy and three contiguous copies of T-DNA, respectively, were inserted in the second intron of NRT1.7 gene (FIG. 7A). No expression of NRT1.7 mRNA and protein could be detected by RT-PCR (data not shown) and Western blot analysis (FIG. 7B) showing that both are null mutants.

The nitrate content in each leaf was analyzed in wild type and mutants. Compared to the wild type, higher amounts of nitrate accumulated in old leaves of the mutants (FIGS. 7C and 7D). Preferential expression of NRT1.7 in old leaves and accumulation of nitrate in the old leaves of the mutants suggest that NRT1.7 is responsible for remobilizing nitrate from the old leaves to other tissues.

Figure 8:
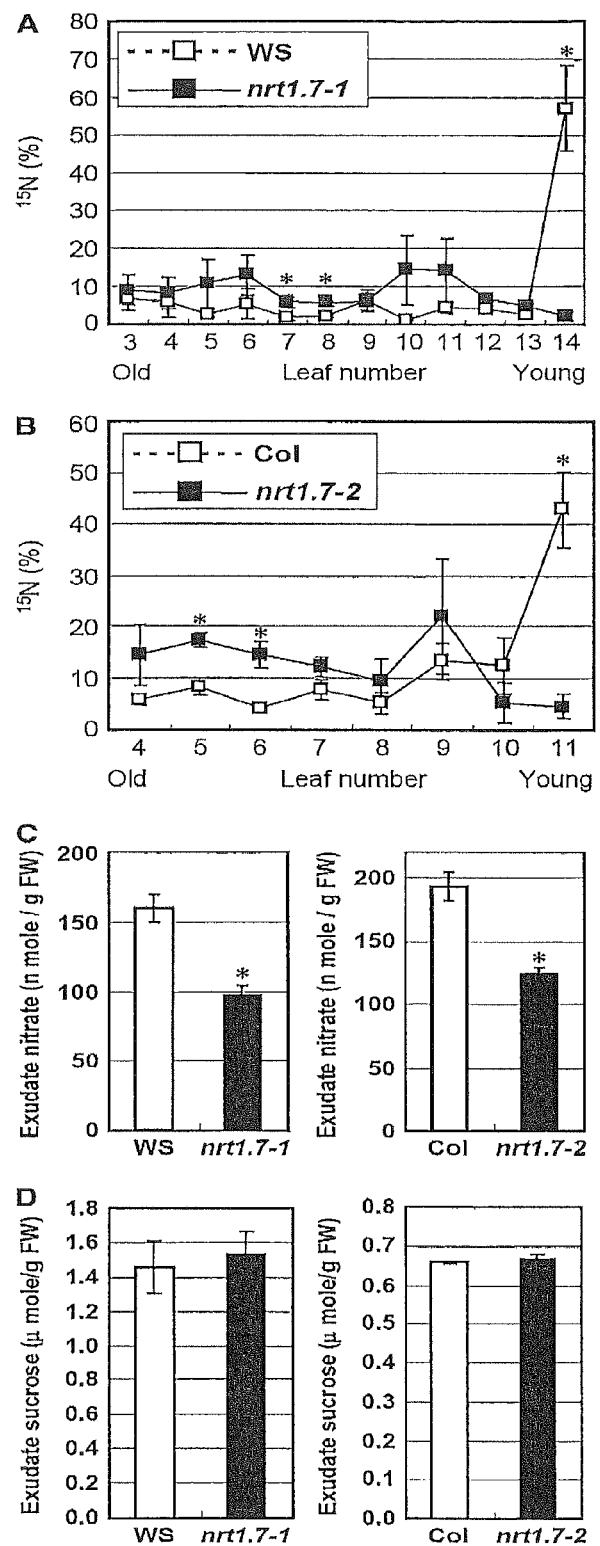
FIG. 8A and FIG. 8B are diagrams showing nitrate remobilization from old leaves to young leaves are defected in nrt1.7 mutants and $^{15}N$-nitrate tracing assay in the wild type and mutants; wherein the amount of $^{15}N$ in each leaf is presented as the percentage of total $^{15}N$ in rosette leaves; the values are mean±SE of three independent plants; and * represents significant difference ($p<0.01$) between the wild types and mutants.
FIG. 8C is a diagram showing nitrate contents in phloem exudates; wherein the nitrate contents in phloem exudates of old leaf were lower in nrt1.7 mutants; the values are mean±SE of three biological repeats; and * represents significant difference ($p<0.005$) between the wild types and mutants.
FIG. 8D is a diagram showing sucrose contents in phloem exudates; wherein sucrose contents in the same phloem exudates of FIG. 8C were measured; there was no significant difference between the wild types and mutants; an the values were mean±SE of three biological repeats.

Example 6 nrt1.7 Mutants were Defective in Remobilizing $^{15}$N-Nitrate from Old Leaves to Young Leaves and Flower That NRT1.7 functions in nitrate remobilization was further confirmed by a $^{15}$N-nitrate spotting experiment. $^{15}$N-nitrate was spotted on distal parts of the oldest non-senescent leaf, and 20 hours after spotting, $^{15}$N contents of different leaves and organs were analyzed. In the wild type, $^{15}$N-nitrate spotted on the old leaf moved to young leaves; in the mutants, little or no $^{15}$N could be found in the young leaves (FIGS. 8A and 8B). These data indicate that the nitrate transporter NRT1.7 is responsible for remobilizing nitrate from older leaves to N-demanding tissues, such as young leaves.

Since NRT1.7 is expressed in the phloem of old leaves, the amount of nitrate in the phloem sap was compared between wild type and mutants. In a slight modification of an older protocol (Deeken et al., 2008, Plant J 55, 746-759), the third and fourth leaves were cut, recut in EDTA buffer, washed and then placed into tubes with 200 µl EDTA buffer. After phloem bleeding for 1 h, the buffer solution, which contained diluted phloem sap, was used for composition analyses. The glucose content in the phloem exudates was lower than the detection limit (50 nmole/g fresh weight [FW]), suggesting that the concentration of damaged cell extract in the exudates was low. Nitrate contents in the exudates were 159.9±9.7 n mole/g FW in WS, 96.8±7.4 in nrt1.7-1; 193.2±11.5 in Col, and 123.9±5.0 in nrt1.7-2 (FIG. 8C) indicating that compared to wild type, the nitrate contents of phloem exudates in nrt1.7 mutants decreased 35~40%. Other types of transporters or loading mechanisms could be responsible for the remaining nitrate detected in the phloem sap of the nrt1.7 mutants. The sucrose content in the mutants is comparable to the values of their corresponding wild types (FIG. 8D), suggesting that reduced nitrate content in the mutants is not due to reduced exudation rate of phloem sap in the mutants.

Example 7

Growth Retardation in nrt1.7 Mutants During Nitrogen Starvation

Figure 9:
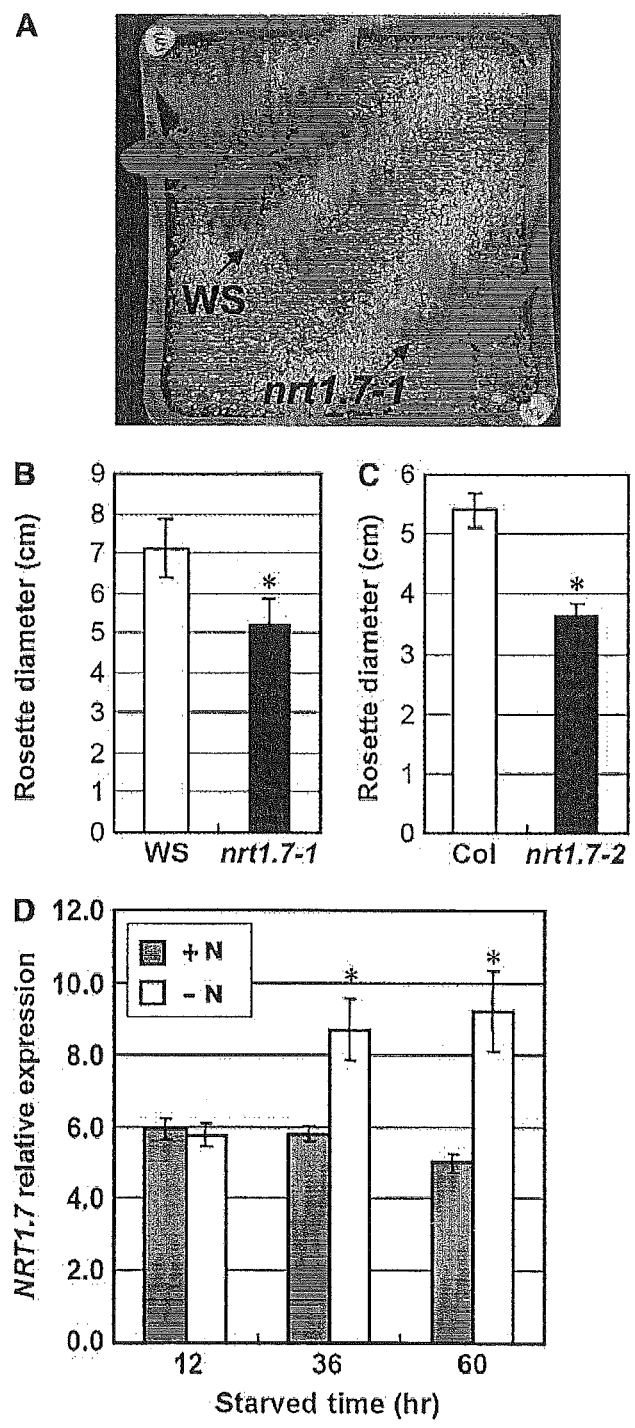
FIG. 9A is an image showing representative 35 days old plants grown with full nutrients for 10 days and then nitrogen starved for 25 days.
FIG. 9B and FIG. 9C are diagrams showing rosette size of the wild type and nrt1.7 mutants under nitrogen starvation; wherein the values were mean SD; n=5 for Ws/nrt1.7-1, and n=4 for Col/nrt1.7-2' and the plants were grown with full nutrients for 10 days and the nitrogen starved for 25 days for Ws background and 15 days for Col background; and * represents significant difference ($p<0.005$) between the wild types and mutants.
FIG. 9D is a diagram showing quantitative RT-PCR analysis of NRT1.7 expression in nitrogen starved plants; wherein the plants were grown hydroponically for 34 days with full nutrients and then shifted to nitrogen-depleted medium for the time indicated; the relative expression level was the expression of NRT1.7 normalized to that of UBQ10; the values are mean±SE of three biological repeats; and * represents Significant difference ($p<0.005$) between the wild types and mutants.

Under nutrient-sufficient conditions, no growth difference was seen between mutants and wild type. However, when plants were starved of nitrogen at an early stage (10 days after germination), compared to wild type, both nrt1.7 mutants showed growth retardation (FIG. 9A). When compared with the wild type grown in the same pots, the mutant rosettes were about 30% smaller in diameter (FIGS. 9B and 9C). Quantitative RT-PCR analysis revealed that NRT1.7 expression was induced by nitrogen starvation (FIG. 9D). The growth retardation found in mutants and enhanced expression of NRT1.7 by nitrate starvation suggests that nitrate remobilization is important to sustain vigorous growth under nitrogen-starvation conditions.

Example 8

Preparation of Transgenic Plants Overexpressing NRT1.7 Protein to Enhance the Growth According to the studies of Example 8, nrt1.7 gene mutation can result in the growth retardation of the transgenic plant. From this fact, it reasonably deduces that overexpression of NRT1.7 in a plant might enhance nitrate remobilization thereby the growth of the plant is enhanced and resistant to nitrogen starvation.

To this aim, i.e., the expression of NRT1.7 can be put under the control of its own promoter operatedly linked with 35S enhancer (see Weigel et al., Plant Physiol. 122(4):1003-1013. 2000, April). Plant transformation was performed as described (Clough et al, 1998, Plant J 16, 735-743). Briefly, NRT1.7 promoter was eluted from NRT1.7 promoter-GUS by digesting with BamHI and XbaI as described above. NRT1.7 cDNA was generated by PCR using pGEMHE-At-NRT1.7 as the template and the primers forward 5'-AT-CAAGCTTGCTCTAGAG-3' (SEQ ID NO: 38) and reverse 5'-GGGATCCAGATGGTTTTGGA-3' (SEQ ID NO: 39). The PCR product was cut with XbaI and BamHI. The XbaI ligated fragment containing NRT1.7::NRT1.7 was inserted into a mini-binary vector pCB302 for transform into *Arabidopsis* Col wild type and nrt1.7-2. Another binary vector, pSKI015, with 4×35S enhancer (SEQ ID NO: 4) was digested with SpeI and ligated with the XbaI fragment containing NRT1.7::NRT1.7 to obtain an expression vector. A transgenic plant overexpression of NRT1.7 shall be obtainable by transforming this expression vector in which.

Example 9

AtNRT1.1 and AtNRT1.2 Fused Protein (NC4N) Exhibiting Greater Transport Activity To determine the transport activity of the fused protein (NC4N) in vivo, a full length cDNA fragment encoding AtNRT1.1 and AtNRT1.2 fused protein was cloned into the pGEMHE vector to generate pGEMHE-NC4N. The pGEMHE-NC4N was linearized using NheI, and capped mRNA was transcribed in vitro using mMESSAGE mMACHINE kits (Ambion). Oocytes were injected with 50 ng of NC4N cRNA as described previously. Nitrate uptake assays using 10 mM $^{15}$N-nitrate were performed as described previously using a continuous-flow isotope ratio mass spectrometer coupled with a carbon nitrogen elemental analyzer, and oocytes injected with NRT1.1 cRNA or water ($H_2O$) were used as a positive or negative control, respectively. The result was shown in the FIG. 10. The values are mean±SD; n=5 for water- and NRT1.1 cRNA-injected oocytes, and n=4 for NC4N cRNA-injected oocytes. * represents significant difference (p<0.001) between the cRNA-injected and water-injected oocytes. # represents significant difference (p<0.05) between the NRT1.1 cRNA-injected oocytes and NC4N cRNA-injected oocytes.

Figure 10:
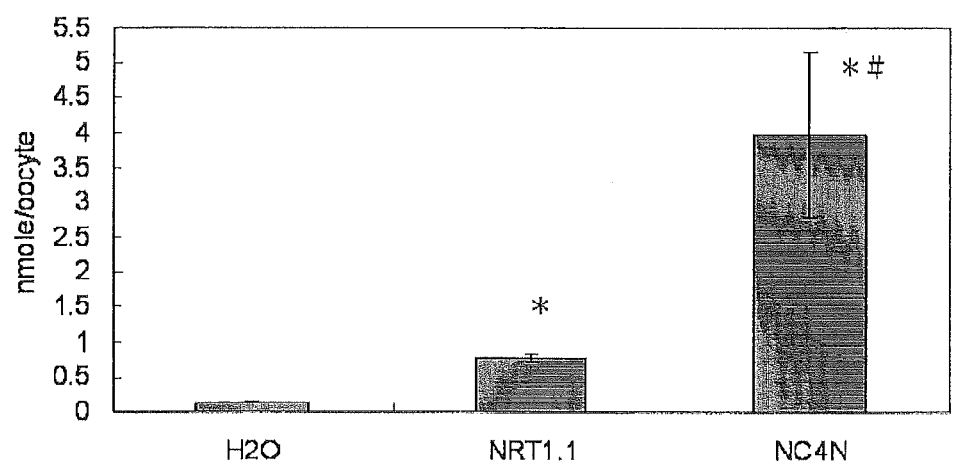
FIG. 10 is a diagram showing a diagram showing the Low-affinity nitrate uptake activity of NRT1.1-, NC4N- or water-injected oocytes; and the values are means±SD (n=5 for water- and NRT1.1 cRNA-injected oocytes, and n=4 for NC4N cRNA-injected oocytes); and * represents significant difference ($p<0.001$) between the cRNA-injected and water-injected oocytes; # represents significant difference ($p<0.05$) between the NRT1.1 cRNA-injected oocytes and NC4N cRNA-injected oocytes); and "NC4N" means the chimera gene encoding AtNRT1.1 and AtNRT1.2 fused protein.

As shown in FIG. 10, both NRT1.1 cRNA-injected oocytes and NC4N cRNA-injected oocytes were found to take up more nitrate than water-injected oocytes. Moreover, NC4N cRNA-injected oocytes were found to take up more nitrates than NRT1.1 cRNA-injected oocytes. This result suggests that the chimera fused protein of the present invention has better transport activity than any known NRT transports. One can expect to enhance growth or resistance to nitrogen starvation of a plant by transforming such chimera gene with said plant.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An isolated nucleic acid molecule, comprising a nucleic acid sequence encoding a chimera nitrate transporter protein that has the amino acid sequence of SEQ ID NO:11.

2. The isolated nucleic acid molecule of claim 1, wherein the nucleic acid sequence has the sequence of SEQ ID NO:10.

3. An expression construct, comprising the nucleic acid molecule of claim 1, wherein the nucleic acid sequence is operably linked to a promoter.

4. The expression construct of claim 3, wherein the promoter sequence is an *Arabidopsis* NRT1.7 promoter.

5. The expression construct of claim 4, wherein the promoter has the sequence of SEQ ID NO:3.

6. The expression construct of claim 4, further comprising an enhancer.

7. The expression construct of claim 6, wherein the enhancer is a CaMV 35S enhancer.

8. The expression construct of claim 7, wherein the enhancer has the sequence of SEQ ID NO:4.

9. The expression construct of claim 6, wherein the enhancer is operably linked to the promoter.

10. A transgenic plant transformed with an expression construct, the expression construct containing a nucleic acid sequence that encodes a chimera nitrate transporter protein having the amino acid sequence of SEQ ID NO:11, wherein the nucleic acid sequence is operably linked to a promoter and the protein is expressed in the transgenic plant.

11. The transgenic plant of claim 10, wherein the promoter is an *Arabidopsis* NRT1.7 promoter.

12. The transgenic plant of claim 11, wherein the promoter has the sequence of SEQ ID NO:3.

13. The transgenic plant of claim 11, wherein the expression construct further contains an enhancer.

14. The transgenic plant of claim 13, wherein the enhancer is a CaMV 35S enhancer.

15. The transgenic plant of claim 10, wherein the transgenic plant exhibits improved nitrogen utilization efficiency as compared to a wild-type plant not transformed with the expression construct.

16. The transgenic plant of claim 10, wherein the nucleic acid sequence has the sequence of SEQ ID NO:10.

17. A method of producing a transgenic plant with improved nitrogen utilization efficiency, the method comprising:

transforming a plant with an expression construct, wherein the expression construct contains a nucleic acid sequence that encodes a chimera nitrate transporter protein that has the amino acid sequence of SEQ ID NO:11, the nucleic acid sequence being operably linked to a promoter, thereby a transgenic plant that expresses the protein and exhibits improved nitrogen utilization efficiency as compared to an untransformed plant is produced.

18. The method of claim 17, wherein the promoter is an *Arabidopsis* NRT1.7 promoter.

19. The method of claim 17, wherein the promoter has the sequence of SEQ ID NO:3.

20. The method of claim 17, wherein the expression construct further contains an enhancer.

* * * * *